US012760336B2

(12) United States Patent
Lynch et al.

(10) Patent No.: US 12,760,336 B2
(45) Date of Patent: Oct. 13, 2026

(54) METHODS AND COMPOSITIONS FOR THE PRODUCTION OF ACETYL-COA DERIVED PRODUCTS

(71) Applicant: Duke University, Durham, NC (US)

(72) Inventors: Michael David Lynch, Durham, NC (US); Shuai Li, Durham, NC (US)

(73) Assignee: Duke University, Durham, NC (US)

( * ) Notice: Subject to any disclaimer, the term of this patent is extended or adjusted under 35 U.S.C. 154(b) by 736 days.

(21) Appl. No.: 18/006,506

(22) PCT Filed: Jul. 23, 2021

(86) PCT No.: PCT/US2021/043023

§ 371 (c)(1),
(2) Date: Jan. 23, 2023

(87) PCT Pub. No.: WO2022/020748

PCT Pub. Date: Jan. 27, 2022

(65) Prior Publication Data

US 2023/0227864 A1 Jul. 20, 2023

Related U.S. Application Data

(60) Provisional application No. 63/056,031, filed on Jul. 24, 2020.

(51) Int. Cl.

| | |
|---|---|
| ***C12N 1/19*** | (2006.01) |
| ***C12N 9/02*** | (2006.01) |
| ***C12N 9/04*** | (2006.01) |
| ***C12N 9/10*** | (2006.01) |
| ***C12N 15/11*** | (2006.01) |
| ***C12N 15/63*** | (2006.01) |
| ***C12N 15/70*** | (2006.01) |
| ***C12P 7/44*** | (2006.01) |

(52) U.S. Cl.

CPC .............. *C12P 7/44* (2013.01); *C12N 9/0006* (2013.01); *C12N 9/0008* (2013.01); *C12N 9/0067* (2013.01); *C12N 9/1025* (2013.01); *C12N 15/11* (2013.01); *C12N 15/635* (2013.01); *C12N 15/70* (2013.01); *C12Y 101/01049* (2013.01); *C12Y 102/04001* (2013.01); *C12Y 112/07002* (2013.01); *C12Y 203/03001* (2013.01); *C12N 2310/20* (2017.05); *C12N 2800/101* (2013.01); *C12N 2830/001* (2013.01)

(58) Field of Classification Search

CPC ....... C12P 7/44; C12N 9/1025; C12N 9/0006; C12N 9/0008; C12N 9/0067; C12N 15/70; C12N 15/11; C12N 15/635; C12N 2310/20; C12N 2800/10; C12N 2830/001; C12Y 203/03001; C12Y 101/01049; C12Y 102/04001; C12Y 112/07002

See application file for complete search history.

(56) References Cited

U.S. PATENT DOCUMENTS

| | | | |
|---|---|---|---|
| 2014/0004597 | A1 | 1/2014 | Chang et al. |
| 2019/0093135 | A1 | 3/2019 | Wu et al. |

FOREIGN PATENT DOCUMENTS

| | | | |
|---|---|---|---|
| CN | 101469317 | A | 7/2009 |
| CN | 107208118 | A | 9/2017 |
| CN | 110536960 | B | 12/2019 |
| JP | 2010-527239 | A | 8/2010 |
| JP | 2017-523780 | A | 8/2017 |
| JP | 2018-500002 | A | 1/2018 |
| WO | 2013184602 | A2 | 12/2013 |
| WO | 2014057008 | A1 | 4/2014 |
| WO | 2016044713 | A1 | 3/2016 |
| WO | 2016053397 | A2 | 4/2016 |
| WO | 2017165397 | A1 | 9/2017 |
| WO | 2018156646 | A1 | 8/2018 |
| WO | 2020061385 | A1 | 3/2020 |

OTHER PUBLICATIONS

International Search Report and Written Opinion issued in PCT Application PCT/US2021/043023, mailing date Dec. 30, 2021.
Sonderegger et al., "Selection of quiescent *Escherichia coli* with high metabolic activity", Metabolic Engineering, vol. 7 p. 4-9, Jan. 7, 2005.
Parimi et al., "Eliminating acetate formation improves citramalate production by metabolically engineered *Escherichia coli*", Microbial Cell Factories, vol. 16, No. 114, p. 1-10, 2017.
Chervaux et al., "Physiological Study of *Lactobacillus delbrueckii* subsp. *bulgaricus* Strains in a Novel Chemically Defined Medium", vol. 66, No. 12, p. 5306-5311, Dec. 2000.
International Preliminary Report on Patentability issued in PCT Application PCT/US2021/043023, dated Nov. 30, 2022.
Written Opinion issued in Singapore Patent Application No. 11202300433U, dated Jul. 30, 2025.
Office Action issued in Chinese Patent Application No. 202180061788.5, dated Nov. 8, 2024.
Office Action issued in Canadian Patent Application No. 3, 189,923, dated Nov. 8, 2024.
Notice of Acceptance issued in Australian Patent Application No. 2021312935, dated Nov. 18, 2024.
Office Action issued in Russian Federation Patent Application No. 2023103347, dated Dec. 23, 2025.
Office Action issued in Russian Patent Application No. 2023103347, mailing date May 13, 2025.
Office Action issued in Japanese Patent Application No. 2023103347, mailing date May 16, 2025.
Parimi, N. S., et al., "Eliminating acetate formation improves citramalate production by metabolically engineered Escherichia coli", Microb. Cell Fact., 2017, 16:114.

(Continued)

*Primary Examiner* — Jennifer E Graser

(74) *Attorney, Agent, or Firm* — Benesch Friedlander Coplan & Aronoff LLP

(57) ABSTRACT

The present disclosure is related to genetically engineered microbial strains and related bioprocesses for the production of products from acetyl-CoA. Specifically, the use of dynamically controlled synthetic metabolic valves to reduce the activity of certain enzymes, leads to increased product production in a two-stage process.

17 Claims, 15 Drawing Sheets

Specification includes a Sequence Listing.

(56) References Cited

OTHER PUBLICATIONS

Chang, Y., et al., "Easy regulation of metabolic flux in *Escherichia coli* using an endogenous type I-E CRISPR-Cas system", Microb. Cell Fact., 2016, 15:195.
McGinness, K. E., et al., " Engineering Controllable Protein Degradation", Molecular Cell, 2006, vol. 22, pp. 701-707.
Webb, J., et al., "Efficient bio-production of citramalate using an engineered *Escherichia coli* strain", Microbiology, 2018, vol. 164, No. 2, pp. 133-141.
Nakayam, T., et al., "*Escherichia coli* pyruvate: flavodoxin oxidoreductase, YdbK—regulation of expression and biological roles in protection against oxidative stress", Genes Genet. Syst., 2013, vol. 88, pp. 175-188.
Rungrassamee, W., et al., "Activation of glucose transport under oxidative stress in *Escherichia coli*", Arch. Microbiol., 2008, vol. 190, pp. 41-49.
Moreb. E. A., "Media Robustness and Scalability of Phosphate Regulated Promoters Useful for Two-Stage Autoinducation in *E. coli*", ACS, Synthetic Biology, 2020, 9, 1483-1486.
Office Action issued in Chinese Patent Application No. 202180061788.5, mailing date May 30, 2025.
Examination Report issued in Australian Patent Application No. 2021312935, dated Dec. 5, 2023.
Supplementary European Search Report issued in European Patent Application No. 21845860.2, dated Jan. 24, 2024.
Webb, Joseph P., et al., "Efficient bio-production of citramalate using an engineered Escherichia coli strain", MICROBIOLOGY, vol. 164, No. 2, Feb. 1, 2018.
Webb, Joseph, et al."Systems Analyses Reveal the Resilience of *Escherichia coli* Physiology during Accumulation and Export of the Nonnative Organic Acid Citramalate", mSystems, Jun. 11, 2019.
Hossain, Abeer H., et al., "Identification of novel citramalate biosynthesis pathways in Aspergillus niger", Fungal Biology and Biotechnology, vol. 6, No. 1, Dec. 1, 2019.
Li, Shuai, et al., "Dynamic control over feedback regulation identifies pyruvate-ferredoxin oxidoreductase as a central metabolic enzyme in stationary phase *E . coli*", bioRxiv, Aug. 10, 2020.
Ye, Zhixia, et al., "Two-stage dynamic deregulation of metabolism improves process robustness & scalability in engineered *E. coli*", Metabolic Engineering, Academic Press, Amsterdam, NL, vol. 68, Sep. 30, 2021.
Communication Pursuant to Article 94(3) EPC issued in European Patent Application No. 21845860.2, dated Feb. 5, 2024.
Written Opinion issued in Singapore Patent Application No. 11202300433U, dated Feb. 20, 2024.
Modified Substantive Examination Report issued in Malaysian Patent Application No. PI2023000320 dated Nov. 14, 2025.
Decision of Rejection issued in Japanese Patent Application No. 2023-504117 dated Dec. 9, 2025.
Office Action issued in Russian Patent Application No. 2023103347/10, dated Jan. 19, 2026.
Litvitsky, p. F., "Heredity, variability and pathology", VSP, 2012, N3, pp. 18-27. Retrieved from the Internet Apr. 18, 2026, URL: https://cyberleninka.ru/article/n/nasledstvennost-izmenchivost-i-patologiya.
Wu, X., et al., "Producation of citramalate by metabolically engineered *Escherichia coli*", Biotechnology and bioengineering, vol. 113, 12 (2016): 2670-2675.

METHODS AND COMPOSITIONS FOR THE PRODUCTION OF ACETYL-COA DERIVED PRODUCTS

CROSS-REFERENCE TO RELATED APPLICATIONS

This application claims priority to U.S. Provisional Patent Application No. 63/056,031 filed Jul. 24, 2020 which is incorporated by reference herein in its entirety.

FEDERALLY SPONSORED RESEARCH OR DEVELOPMENT

This invention was made with government support under NSF EAGER: #1445726, DARPA #HR0011-14-C-0075, ONR YIP #N00014-16-1-2558, DOE EERE grant #EE0007563. The government has certain rights in the invention.

FIELD OF THE INVENTION

This invention relates to metabolically engineered microorganisms, such as bacterial strains, and bioprocesses utilizing such strains. These strains provide dynamic control of metabolic pathways resulting in the production of products from acetyl-CoA.

SEQUENCE LISTING

The instant application contains a Sequence Listing which has been filed electronically in ASCII format as 49186-48_ST25.txt created Jul. 13, 2021 that is 26,740 bytes in size and is hereby incorporated by reference in its entirety.

BACKGROUND OF THE INVENTION

Biotechnology based fermentation processes have made rapid advancements in recent years due to technology developments in the fields of fermentation science and synthetic biology, as well as metabolic and enzyme engineering. However improvements in rates, titers and yields are often needed to enable commercially competitive processes. Most metabolic engineering strategies aimed at improving these metrics rely on the overexpression of desired pathway enzymes and deletion and/or downregulation of competing biochemical activities. Over the last several decades, stoichiometric models of metabolism have helped to move the field from manipulating gene expression levels to manipulating networks, which can now be designed to couple growth with product formation, and selection can be used to optimize for both.

A remaining limitation of these approaches are the metabolic boundary conditions required for cellular growth. Dynamic metabolic control and specifically two-stage control offer a potential engineering strategy to overcome these limitations, by switching to a production state where metabolite and enzyme levels can be pushed past the boundaries required for growth. Significant efforts have been made to develop tools for dynamic metabolic control including control systems, metabolic valves and modeling approaches. However to date, previous work has largely focused on dynamically redirecting fluxes by switching "OFF" pathways that stoichiometrically compete with a desired pathway.

SUMMARY OF THE INVENTION

We demonstrate increased stationary phase flux attributable to dynamic reduction in metabolites which act as feedback regulators of central metabolism, and not reductions in competing metabolic pathways. Employing two-stage dynamic metabolic control we describe manipulating feedback regulation in central metabolism and improve biosynthesis in genetically modified microorganisms. Specifically, we describe the impact of dynamic control over two central metabolic enzymes: citrate synthase, and glucose-6-phosphate dehydrogenase, on stationary phase fluxes. Reduced citrate synthase levels lead to a reduction in α-ketoglutarate, which is an inhibitor of sugar transport, resulting in increased glucose uptake and glycolytic fluxes.

Other methods, features and/or advantages is, or will become, apparent upon examination of the following Figures and detailed description. It is intended that all such additional methods, features, and advantages be included within this description and be protected by the accompanying claims.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are used, and the accompanying drawings of which:

DETAILED DESCRIPTION OF THE INVENTION

Figure 1:
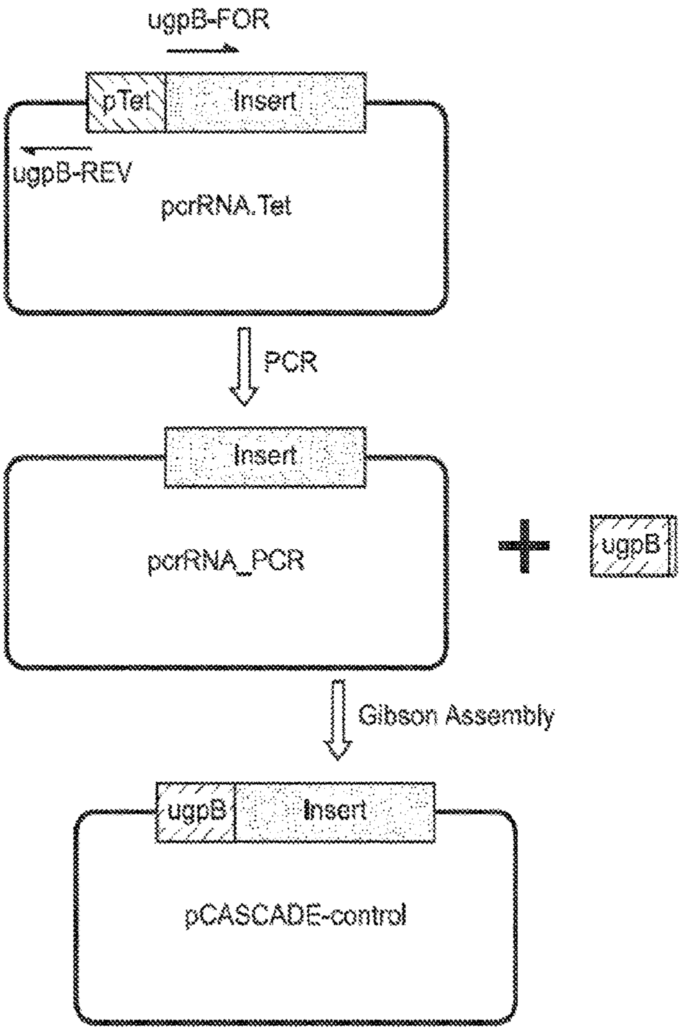
FIG. 1 depicts a schematic of pCASCADE-control plasmid construction scheme.

Demonstrated herein is the use of two-stage dynamic metabolic control to manipulate feedback regulation in central metabolism and improve biosynthesis in engineered *E. coli*. Specifically, we report the impact of dynamic control over two central metabolic enzymes: citrate synthase, and glucose-6-phosphate dehydrogenase, on stationary phase fluxes. Firstly, reduced citrate synthase levels lead to a reduction in α-ketoglutarate, which is an inhibitor of sugar transport, resulting in increased glucose uptake and glycolytic fluxes. Reduced glucose-6-phosphate dehydrogenase activity activates the SoxRS regulon and expression of pyruvate-ferredoxin oxidoreductase, which is in turn responsible for large increases in acetyl-CoA production. These two mechanisms lead to the improved stationary phase production of citramalic acid enabling titers of 126±7 g/L. These results identify pyruvate oxidation via the pyruvate-ferredoxin oxidoreductase as a "central" metabolic pathway in stationary phase and highlight the potential of improving fluxes by manipulating essential central regulatory mechanisms using two-stage dynamic metabolic control

Definitions

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

The term "heterologous DNA," "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as a nonnative promoter driving gene expression.

The term "synthetic metabolic valve," and the like as used herein refers to either the use of controlled proteolysis, gene silencing or the combination of both proteolysis and gene silencing to alter metabolic fluxes.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome). As used herein, chromosomal and native and endogenous refer to genetic material of the host microorganism.

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production, Micro-fermentation (microfermentation) or Fermentation, as used herein, may be aerobic, microaerobic, or anaerobic.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a UniProt identification number, which would be well known to one skilled in the art. The UniProt database can be accessed at UniProt.org. When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

The meaning of abbreviations is as follows: "C" means Celsius or degrees Celsius, or ° C. as is clear from its usage, DCW means dry cell weight, "s" means second(s), "min" means minute(s), "h," "hr," or "hrs" means hour(s), "psi" means pounds per square inch, "nm" means nanometers, "d" means day(s), "µL" or "uL" or "ul" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "µmol" or "uMol" means micromole(s)", "g" means gram(s), "µg" or "ug" means microgram(s) and "ng" means nanogram(s), "PCR" means polymerase chain reaction, "OD" means optical density, "$OD_{600}$" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-µ-thiogalactopyranoiside, "aTc" means anhydrotetracycline, "RBS" means ribosome binding site, "rpm" means revolutions per minute, "HPLC" means high performance liquid chromatography, and "GC" means gas chromatography.

I. Carbon Sources

Bio-production media, which is used in the present invention with recombinant microorganisms must contain suitable carbon sources or substrates for both growth and production stages. Suitable substrates may include, but are not limited to glucose, or a combination of xylose, glucose, sucrose, xylose, mannose, arabinose, oils, carbon dioxide, carbon monoxide, methane, methanol, formaldehyde or glycerol. It is contemplated that all of the above mentioned carbon substrates and mixtures thereof are suitable in the present invention as a carbon source(s).

II. Microorganisms

Features as described and claimed herein may be provided in a microorganism selected from the listing herein, or another suitable microorganism, that also comprises one or more natural, introduced, or enhanced product bio-production pathways. Thus, in some embodiments the microorganism(s) comprise an endogenous product production pathway (which may, in some such embodiments, be enhanced), whereas in other embodiments the microorganism does not comprise an endogenous product production pathway.

More particularly, based on the various criteria described herein, suitable microbial hosts for the bio-production of a chemical product generally may include, but are not limited to the organisms described in the Common Methods Section.

The host microorganism or the source microorganism for any gene or protein described here may be selected from the following list of microorganisms: *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces*, and *Pseudomonas*. In some aspects the host microorganism is an *E. coli* microorganism.

III. Media and Culture Conditions

In addition to an appropriate carbon source, such as selected from one of the herein-disclosed types, bio-production media must contain suitable minerals, salts, cofactors, buffers and other components, known to those skilled in the art, suitable for the growth of the cultures and promotion of chemical product bio-production under the present invention.

Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media are well characterized and known in the art. Suitable pH ranges for the bio-production are between pH 2.0 to pH 10.0, where pH 6.0 to pH 8.0 is a typical pH range for the initial condition. However, the actual culture conditions for a particular embodiment are not meant to be limited by these pH ranges. Bio-productions may be performed under aerobic, microaerobic or anaerobic conditions with or without agitation.

IV. Bio-Production Reactors and Systems

Fermentation systems utilizing methods and/or compositions according to the invention are also within the scope of the invention. Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering.

The amount of a product produced in a bio-production media generally can be determined using a number of methods known in the art, for example, high performance liquid chromatography (HPLC), gas chromatography (GC), or GC/Mass Spectroscopy (MS).

V. Genetic Modifications, Nucleotide Sequences, and Amino Acid Sequences

Embodiments of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as *E. coli*, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various embodiments of the invention the genetic manipulations may include a manipulation directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected culture conditions. Genetic manipulation of nucleic acid sequences may increase copy number and/or comprise use of mutants of an enzyme related to product production. Specific methodologies and approaches to achieve such genetic modification are well known to one skilled in the art.

In various embodiments, to function more efficiently, a microorganism may comprise one or more gene deletions. For example, in *E. coli*, the genes encoding the lactate dehydrogenase (ldhA), phosphate acetyltransferase (pta), pyruvate oxidase (poxB), pyruvate-formate lyase (pflB), methylglyoxal synthase (mgsA), acetate kinase (ackA), alcohol dehydrogenase (adhE), the clpXP protease specificity enhancing factor (sspB), the ATP-dependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various embodiments. Gene deletions may be accomplished by numerous strategies well known in the art, as are methods to incorporate foreign DNA into a host chromosome.

In various embodiments, to function more efficiently, a microorganism may comprise one or more synthetic metabolic valves, composed of enzymes targeted for controlled proteolysis, expression silencing or a combination of both controlled proteolysis and expression silencing. For example, one enzyme encoded by one gene or a combination of numerous enzymes encoded by numerous genes in *E. coli* may be designed as synthetic metabolic valves to alter metabolism and improve product formation. Representative genes in *E. coli* may include but are not limited to the following: fabI, zwf, gltA, ppc, udhA, lpd, sucD, aceA, pfkA, lon, rpoS, pykA, pykF, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms.

Accordingly, as described in various sections above, some compositions, methods and systems of the present invention comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications.

In addition to the above-described genetic modifications, in various embodiments genetic modifications, including synthetic metabolic valves also are provided to increase or decrease the pool and availability of a cofactor such as NADPH and/or NADH which may be consumed in the production of a product.

VI. Synthetic Metabolic Valves

Use of synthetic metabolic valves allows for simpler models of metabolic fluxes and physiological demands during a production phase, turning a growing cell into a stationary phase biocatalyst. These synthetic metabolic valves can be used to turn off essential genes and redirect carbon, electrons and energy flux to product formation in a multi-stage fermentation process. One or more of the following provides the described synthetic valves: 1) transcriptional gene silencing or repression technologies in combination with 2) inducible and selective enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

In particular, the invention describes the construction of synthetic metabolic valves comprising one or more or a combination of the following: controlled gene silencing and controlled proteolysis. It is appreciated that one well skilled in the art is aware of several methodologies for gene silencing and controlled proteolysis.

VI.A Gene Silencing

In particular, the invention describes the use of controlled gene silencing to provide the control over metabolic fluxes in controlled multi-stage fermentation processes. There are several methodologies known in the art for controlled gene silencing, including but not limited to mRNA silencing or RNA interference, silencing via transcriptional repressors and CRISPR interference. Methodologies and mechanisms for RNA interference are taught by Agrawal et al. "RNA Interference: Biology, Mechanism, and Applications" Microbiology and Molecular Biology Reviews, December 2003; 67(4) p 657-685. DOI: 10.1128/MMBR.67.657-685.2003. Methodologies and mechanisms for CRISRPR interference are taught by Qi et al. "Repurposing CRISPR as an RNA-guided platform for sequence-specific control of gene expression" Cell February 2013; 152(5) p 1173-1183. DOI: 10.1016/j.ce11.2013.02.022. In addition, methodologies and mechanisms for CRISRPR interference using the native *E. coli* CASCADE system are taught by Luo et al. "Repurposing endogenous type I CRISPR-Cas systems for programmable gene repression" NAR. October 2014; DOI: 10.1093. In additional numerous transcriptional repressor systems are well known in the art and can be used to turn off gene expression.

VI.B Controlled Proteolysis

In particular, the invention describes the use of controlled protein degradation or proteolysis to provide the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the *E. coli* clpXP protease for controlled protein degradation are taught by McGinness et al, "Engineering controllable protein degradation", Mol Cell. June 2006; 22(5) p 701-707. This methodology relies upon adding a specific C-terminal peptide tag such as a DAS4 (or DAS+4) tag. Proteins with this tag are not degraded by the clpXP protease until the specificity enhancing chaperone sspB is expressed. sspB induces degradation of DAS4 tagged proteins by the clpXP protease. In additional numerous site specific protease systems are well known in the art. Proteins can be engineered to contain a specific target site of a given protease and then cleaved after the controlled expression of the protease. In some embodiments, the cleavage can be expected lead to protein inactivation or degradation. For example Schmidt et al ("ClpS is the recognition component for *Escherichia coli* substrates of the N-end rule degradation pathway" Molecular Microbiology March 2009. 72(2), 506-517. doi:10.1111), teaches that an N-terminal sequence can be added to a protein of interest in providing clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus. The preference of using an N-terminal vs. C-terminal tag will largely depend on whether either tag affects protein function prior to the controlled onset of degradation.

The invention describes the use of controlled protein degradation or proteolysis to provide the control over metabolic fluxes in controlled multi-stage fermentation processes, in *E. coli*. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host. For example Grilly et al, "A synthetic gene network for tuning protein degradation in *Saccharomyces cerevisiae*" Molecular Systems Biology 3, Article 127. doi:10.1038, teaches the expression and use of the *E. coli* clpXP protease in the yeast *Saccharomyces cerevisiae*. Such approaches can be used to transfer the methodology for synthetic metabolic valves to any genetically tractable host.

VI.C Synthetic Metabolic Valve Control

In particular the invention describes the use of synthetic metabolic valves to control metabolic fluxes in multi-stage fermentation processes. There are numerous methodologies known in the art to induce expression that can be used at the transition between stages in multi-stage fermentations. These include but are not limited to artificial chemical inducers including: tetracycline, anhydrotetracycline, lactose, IPTG (isopropyl-beta-D-1-thiogalactopyranoside), arabinose, raffinose, tryptophan and numerous others. Systems linking the use of these well known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur and magnesium. Natural gene expression systems that respond to these nutrient limitations can be used to operably link the control of gene expression silencing and/or controlled proteolysis to the transition between growth and production phases in multi-stage fermentation processes.

Within the scope of the invention are genetically modified microorganism, wherein the microorganism is capable of producing a product at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

In various embodiments, the invention includes a culture system comprising a carbon source in an aqueous medium and a genetically modified microorganism according to any one of claims herein, wherein said genetically modified organism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10,000 L, greater than 50,000 L, greater than 100,000 L or greater than 200,000 L, and such as when the volume of the aqueous medium is greater than 250 L and contained within a steel vessel.

Overview of Invention Aspects

In one aspect, a genetically modified microorganism that is usable in a biofermentation process is provided, the microorganism including a production pathway comprising at least one enzyme for producing a product from an acetyl CoA precursor. The microorganism, under conditions of depleting of a limiting nutrient from a growth medium in which the genetically modified microorganism is growing, is induced into a stationary phase or non-dividing cellular state. In this stationary phase, pyruvate-flavodoxin/ferredoxin oxidoreductase enzyme activity is increased within the genetically modified microorganism under aerobic or partially aerobic conditions during the stationary phase or non-dividing cellular state to produce an acetyl CoA pool; and further sugar uptake is enhanced within the genetically modified microorganism, when compared to a non-genetically modified microorganism.

In one aspect, the genetically modified microorganism includes a conditionally triggered synthetic metabolic valve that silences gene expression of the citrate synthase (gltA) and/or glucose-6-phosphate-dehydrogenase (zwf) gene(s); or a conditionally triggered synthetic metabolic valve that enables selective proteolysis of the citrate synthase (gltA) and/or glucose phosphate-dehydrogenase (zwf) enzyme(s) and the synthetic metabolic valve(s) of the microorganism are conditionally triggered during the stationary phase or non-dividing cellular state.

In one aspect, the genetically modified microorganism includes a deletion of endogenous poxB and pflB genes.

In one aspect, the increased pyruvate-flavodoxin/ferredoxin oxidoreductase enzyme activity of the genetically modified microorganism is due to overexpression of a gene encoding pyruvate ferredoxin oxidoreductase during the stationary phase or non-dividing cellular state.

In one aspect, the increased pyruvate-flavodoxin/ferredoxin oxidoreductase enzyme activity of the genetically modified microorganism the pyruvate-flavodoxin/ferredoxin oxidoreductase enzyme is encoded by the ydbK gene and the genetically modified microorganism is an *Enterobacter* microorganism.

In one aspect, the increased pyruvate-flavodoxin/ferredoxin oxidoreductase enzyme activity of the genetically modified microorganism is due to induction of the oxidative soxRS regulon during the stationary phase or non-dividing cellular state.

In one aspect, the increased pyruvate-flavodoxin/ferredoxin oxidoreductase enzyme activity of the genetically modified microorganism the increased pyruvate ferredoxin oxidoreductase enzyme activity is increased as the result of reduced NADPH levels within the genetically modified microorganism during the stationary phase or non-dividing cellular state.

In one aspect, the activity of at least one sugar transporter of the genetically modified microorganism causes activity of at least one sugar transporter is increased to enhance sugar uptake.

In one aspect, the activity of at least one sugar transporter of the genetically modified microorganism is the result of constitutive expression of a sugar transporter gene results in increased sugar transporter activity within the genetically modified microorganism.

In one aspect, the activity of at least one sugar transporter of the genetically modified microorganism is the result of conditionally overexpressed during the stationary phase or non-dividing cellular state.

In one aspect, the sugar transporter of the genetically modified microorganism is encoded by a pts gene.

In one aspect, the genetically modified microorganism is an *Enterobacter* microorganism. In one aspect, the microorganism in an *E. coli* microorganism.

In one aspect, the genetically modified microorganism includes citramalate synthase as an enzyme of the production pathway.

In one aspect, a bioprocess for production of a protein product from the genetically modified microorganism is provided. The bioprocess including in a first stage, growing the genetically modified microorganism in a medium and in a second stage, upon depletion of a limiting nutrient from a growth medium, inducing a stationary phase or non-dividing cellular state. The bioprocess, the genetically modified microorganism in the stationary phase or non-dividing cellular state produces product at a rate of 30 g/L or greater.

In another aspect, the bioprocess includes activity of a pyruvate-flavodoxin/ferredoxin oxidoreductase enzyme is caused by overexpression of a gene encoding an active pyruvate ferredoxin oxidoreductase, induction of the oxidative soxRS regulon, reducing NADPH levels, reducing glucose-6-phosphate dehydrogenase levels with a synthetic metabolic valve directed to gene silencing of the zwf gene or selective proteolysis of the glucose-6-phosphate dehydrogenase enzyme, the valve activated in the stationary phase or non-dividing cellular state, or a combination thereof.

In one aspect, the bioprocess, the activity of at least one sugar transporter is increased.

In one aspect, the bioprocess results in citramalate product and an enzyme of the production pathway comprises citramalate synthase, and the bioprocess produces citramalate at or greater than 100 g/L. In one aspect, the citramalate synthase enzyme is encoded by the cimA3.7 gene.

In one aspect, the genetically modified microorganism of the bioprocess includes a plasmid comprising a citramalate synthase gene is operably linked to a low phosphate inducible promotor.

In one aspect, a bioprocess includes the use of a genetically modified microorganism comprises deletion of endogenous poxB and pflB genes.

Disclosed Embodiments Are Non-Limiting

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a FIG. 3A, 4A, 5A unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all subranges therein.

Also, and more generally, in accordance with disclosures, discussions, examples and embodiments herein, there may be employed conventional molecular biology, cellular biology, microbiology, and recombinant DNA techniques within the skill of the art. Such techniques are explained fully in the literature. See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986. These published resources are incorporated by reference herein.

The following published resources are incorporated by reference herein for description useful in conjunction with the invention described herein, for example, methods of industrial bio-production of chemical product(s) from sugar sources, and also industrial systems that may be used to achieve such conversion (Biochemical Engineering Fundamentals, 2nd Ed. J. E. Bailey and D. F. 011 is, McGraw Hill, New York, 1986, e.g.Chapter 9, pages 533-657 for biological reactor design; Unit Operations of Chemical Engineering, 5th Ed., W. L. McCabe et al., McGraw Hill, New York 1993, e.g., for process and separation technologies analyses; Equilibrium Staged Separations, P. C. Wankat, Prentice Hall, Englewood Cliffs, NJ USA, 1988, e.g., for separation technologies teachings).

All publications, patents, and patent applications mentioned in this specification are entirely incorporated by reference herein, including PCT/US2015/035306 filed Jun. 11, 2015 and PCT/US2018/019040, filed Feb. 21, 2018.

EXAMPLES

The examples herein provide some examples, not meant to be limiting. All reagents, unless otherwise indicated, are obtained commercially. Species and other phylogenic identifications are according to the classification known to a person skilled in the art of microbiology, molecular biology and biochemistry.

Common Methods

Media & Reagents

Unless otherwise stated, all materials and reagents were purchased from Sigma (St. Louis, MO). Luria Broth Lennox formulation was used for routine strain and plasmid propagation and construction. FGM1, FGM30, and SM10++ seed media was prepared as previously described Menacho-Melgar et al. (doi: 10.1101/820787). SM10++ and SM10 no phosphate media were prepared as described by Moreb et al. (doi: 10.1021/acssynbio.0c00182). FGM3 media used in biolector studies is detailed in Supplemental Materials. Working antibiotic concentrations were as follows: kanamycin: 35 μg/mL, chloramphenicol: 35 μg/mL, zeocin: 100 μg/mL, blasticidin: 100 μg/mL, spectinomycin: 25 μg/mL, tetracycline: 5 μg/mL.

FGM 3 Media/Media Stock Solutions:

10× concentrated Ammonium-Citrate 30 salts (1 L) by mixing 30 g of $(NH_4)_2SO_4$ and 1.5 g Citric Acid in water with stirring, adjust pH to 7.5 with NaOH. Autoclave and store at room temperature (RT).

10× concentrated Ammonium-Citrate 90 salts (1 L) by mixing 90 g of $(NH_4)_2SO_4$ and 2.5 g Citric Acid in water with stirring, adjust pH to 7.5 with NaOH. Autoclave and store at RT.

1 M Potassium 3-(N-morpholino) propanesulfonic Acid (MOPS), adjust to pH 7.4 with KOH. Filter sterilize (0.2 μm) and store at RT.

0.5 M potassium phosphate buffer, pH 6.8 by mixing 248.5 mL of 1.0 M $K_2HPO_4$ and 251.5 mL of 1.0 M $KH_2PO_4$ and adjust to a final volume of 1000 mL with ultrapure water. Filter sterilize (0.2 μm) and store at RT.

2 M $MgSO_4$ and 10 mM $CaSO_4$ solutions. Filter sterilize (0.2 μm) and store at RT.

50 g/L solution of thiamine-HCl. Filter sterilize (0.2 μm) and store at 4° C.

500 g/L solution of glucose, dissolving by stirring with heat. Cool, filter sterilize (0.2 μm), and store at RT.

500× Trace Metal Stock: Prepare a solution of micronutrients in 1000 mL of water containing 10 mL of concentrated $H_2SO_4$. 0.6 g $CoSO_4 \cdot 7H_2O$, 5.0 g $CuSO_4 \cdot 5H_2O$, 0.6 g $ZnSO_4 \cdot 7H_2O$, 0.2 g $Na_2MoO_4 \cdot 2H_2O$, 0.1 g $H_3BO_3$, and 0.3 g $MnSO4 \cdot H_2O$. Filter sterilize (0.2 μm) and store at RT in the dark.

Prepare a fresh solution of 40 mM ferric sulfate heptahydrate in water, filter sterilize (0.2 μm) before preparing media each time.

Media Components: Prepare the final working medium by aseptically mixing stock solutions based on the following tables in the order written to minimize precipitation, then filter sterilize (with a 0.2 μm filter).

TABLE 1

FGM3 Media, pH 6.8:

| Ingredient | Concentration Stock | Volume in 1 L (mL) | Final Concentration |
|---|---|---|---|
| Ammonium-Citrate 30 Salts, pH 7.5 | 10 X | 100.0 | 1 X |
| Phosphate Buffer, pH 6.8 | 500 mM | 3.6 | 1.80 mM |
| Trace Metals | 500 X | 2.0 | 1 X |

TABLE 1-continued

| FGM3 Media, pH 6.8: | | | |
|---|---|---|---|
| Ingredient | Concentration Stock | Volume in 1 L (mL) | Final Concentration |
| Fe (II) Sulfate | 40 mM | 2.0 | 0.08 mM |
| $MgSO_4$ | 2M | 1.0 | 2.00 mM |
| $CaSO_4$ | 10 mM | 5.0 | 0.05 mM |
| Glucose | 500 g/L | 90.0 | 45.0 g/L |
| MOPS | 1M | 200.0 | 200 mM |
| Thiamine-HCl | 50 g/L | 0.2 | 0.01 g/L |

Modified Strains

TABLE 2

| List of chromosomally modified strains. | | |
|---|---|---|
| Strain | Genotype | Source |
| DLF_R002 | F-, λ-, Δ(araD-araB)567, lacZ4787(del)(::rrnB-3), rph-1, Δ(rhaD-rhaB)568, hsdR514, ΔackA-pta, ΔpoxB, ΔpflB, ΔldhA, ΔadhE, ΔiclR, ΔarcA | Jarboe, *J. Biomed. Biotechnol.* 2010 |
| DLF_R002 | DLF_R002, ΔsspB | this study |
| DLF_Z002 | DLF_Z002, Δcas3::tm-ugpb-sspB-pro-casA | this study |
| DLF_Z01517 | DLF_Z002, Δcas3::tm-pro-casA | this study |
| DLF_Z0043 | DLF_Z0025, gltA-DAS + 4-zeoR | this study |
| DLF_Z0043G | DLF_Z0025, gltA-sfGFP-zeoR | this study |
| DLF_Z0043GD | DLF_Z0025, gltA-sfGFP-DAS + 4-zeoR | this study |
| DLF_Z01002 | DLF_Z0025, zwf-DAS + 4-bsdR | this study |
| DLF_Z01002G | DLF_Z0025, zwf-sfGFP-zeoR | this study |
| DLF_Z01002GD | DLF_Z0025, zwf-sfGFP-DAS + 4-zeoR | this study |
| DLF_Z0044 | DLF_Z0025, gltA-DAS + 4-zeoR, zwf-DAS + 4-bsdR | this study |
| DLF_Z0048 | DLF_Z0025, lpd-DAS + 4-gentR, gltA-DAS + 4-zeoR, zwf-DAS + 4-bsdR | this study |

TABLE 3

| Oligonucleotides utilized for strain construction. | |
|---|---|
| Oligo | Sequence |
| sspB_kan_F | CTGGTACACGCTGATGAACACC (SEQ ID NO: 1) |
| sspB_kan_R | CTGGTCATTGCCATTTGTGCC (SEQ ID NO: 2) |
| sspB_conf_F | GAATCAGAGCGTTCCGACCC (SEQ ID NO: 3) |
| sspB_conf_R | GTACGCAGTTTGCCAACGTG (SEQ ID NO: 4) |
| cas3_tetA_F | AATAGCCCGCTGATATCATCGATAATACTAAAAAAACAGGGAGGCTATT ATCCTAATTTTTGTTGACACTCTATC (SEQ ID NO: 5) |
| cas3_sacB_R | TACAGGGATCCAGTTATCAATAAGCAAATTCATTTGTTCTCCTTCATATG ATCAAAGGGAAAACTGTCCATATGC (SEQ ID NO: 6) |
| cas3_conf_F | CAAGACATGTGTATATCACTGTAATTC (SEQ ID NO: 7) |
| cas3_500dn | GCGATTGCAGATTTATGATTTGG (SEQ ID NO: 8) |
| gltA_conf_F | TATCATCCTGAAAGCGATGG (SEQ ID NO: 9) |
| zwf_conf_F | CTGCTGGAAACCATGCG (SEQ ID NO: 10) |
| bsdR_int_R | GAGCATGGTGATCTTCTCAGT (SEQ ID NO: 11) |
| zeoR_int_R | ACTGAAGCCCAGACGATC (SEQ ID NO: 12) |
| lpd_conf_F | ATCTCACCGTGTGATCGG (SEQ ID NO: 13) |
| gentR_intR | GCGATGAATGTCTTACTACGGA (SEQ ID NO: 14) |

TABLE 4

Synthetic DNA utilized for strain construction.

tetA-sacB Cassette
TCCTAATTTTTGTTGACACTCTATCATTGATAGAGTTATTTTACCACTCCCTATCAGTGATA
GAGAAAAGTGAAATGAATAGTTCGACAAAGATCGCATTGGTAATTACGTTACTCGATGCC
ATGGGGATTGGCCTTATCATGCCAGTCTTGCCAACGTTATTACGTGAATTTATTGCTTCGG
AAGATATCGCTAACCACTTTGGCGTATTGCTTGCACTTTATGCGTTAATGCAGGTTATCTTT
GCTCCTTGGCTTGGAAAAATGTCTGACCGATTTGGTCGGCGCCCAGTGCTGTTGTTGTCAT
TAATAGGCGCATCGCTGGATTACTTATTGCTGGCTTTTTCAAGTGCGCTTTGGATGCTGTA
TTTAGGCCGTTTGCTTTCAGGGATCACAGGAGCTACTGGGGCTGTCGCGGCATCGGTCATT
GCCGATACCACCTCAGCTTCTCAACGCGTGAAGTGGTTCGGTTGGTTAGGGGCAAGTTTTG
GGCTTGGTTTAATAGCGGGGCCTATTATTGGTGGTTTTGCAGGAGAGATTTCACCGCATAG
TCCCTTTTTTATCGCTGCGTTGCTAAATATTGTCACTTTCCTTGTGGTTATGTTTTGGTTCCG
TGAAACCAAAAATACACGTGATAATACAGATACCGAAGTAGGGGTTGAGACGCAATCGA
ATTCGGTATACATCACTTTATTTAAAACGATGCCCATTTTGTTGATTATTTATTTTTCAGCG
CAATTGATAGGCCAAATTCCCGCAACGGTGTGGGTGCTATTTACCGAAAATCGTTTTGGAT
GGAATAGCATGATGGTTGGCTTTTCATTAGCGGGTCTTGGTCTTTTACACTCAGTATTCCA
AGCCTTTGTGGCAGGAAGAATAGCCACTAAATGGGGCGAAAAAACGGCAGTACTGCTCG
GATTTATTGCAGATAGTAGTGCATTTGCCTTTTTAGCGTTTATATCTGAAGGTTGGTTAGTT
TTCCCTGTTTTAATTTTATTGGCTGGTGGTGGGATCGCTTTACCTGCATTACAGGGAGTGAT
GTCTATCCAAACAAAGAGTCATCAGCAAGGTGCTTTACAGGGATTATTGGTGAGCCTTAC
CAATGCAACCGGTGTTATTGGCCCATTACTGTTTGCTGTTATTTATAATCATTCACTACCAA
TTTGGGATGGCTGGATTTGGATTATTGGTTTAGCGTTTTACTGTATTATTATCCTGCTATCG
ATGACCTTCATGTTAACCCCTCAAGCTCAGGGGAGTAAACAGGAGACAAGTGCTTAGTTA
TTTCGTCACCAAATGATGTTATTCCGCGAAATATAATGACCCTCTTGATAACCCAAGAGCA
TCACATATACCTGCCGTTCACTATTATTTAGTGAAATGAGATATTATGATATTTTCTGAATT
GTGATTAAAAAGGCAACTTTATGCCCATGCAACAGAAACTATAAAAAATACAGAGAATG
AAAAGAAACAGATAGATTTTTTAGTTCTTTAGGCCCGTAGTCTGCAAATCCTTTTATGATT
TTCTATCAAACAAAAGAGGAAAATAGACCAGTTGCAATCCAAACGAGAGTCTAATAGAAT
GAGGTCGAAAAGTAAATCGCGCGGGTTTGTTACTGATAAAGCAGGCAAGACCTAAAATGT
GTAAAGGGCAAAGTGTATACTTTGGCGTCACCCCTTACATATTTTAGGTCTTTTTTTATTGT
GCGTAACTAACTTGCCATCTTCAAACAGGAGGGCTGGAAGAAGCAGACCGCTAACACAGT
ACATAAAAAAGGAGACATGAACGATGAACATCAAAAAGTTTGCAAAACAAGCAACAGTA
TTAACCTTTACTACCGCACTGCTGGCAGGAGGCGCAACTCAAGCGTTTGCGAAAGAAACG
AACCAAAAGCCATATAAGGAAACATACGGCATTTCCCATATTACACGCCATGATATGCTG
CAAATCCCTGAACAGCAAAAAAATGAAAAATATCAAGTTCCTGAGTTCGATTCGTCCACA
ATTAAAAATATCTCTTCTGCAAAAGGCCTGGACGTTTGGGACAGCTGGCCATTACAAAAC
GCTGACGGCACTGTCGCAAACTATCACGGCTACCACATCGTCTTTGCATTAGCCGGAGATC
CTAAAAATGCGGATGACACATCGATTTACATGTTCTATCAAAAAGTCGGCGAAACTTCTA
TTGACAGCTGGAAAAACGCTGGCCGCGTCTTTAAAGACAGCGACAAATTCGATGCAAATG
ATTCTATCCTAAAAGACCAAACACAAGAATGGTCAGGTTCAGCCACATTTACATCTGACG
GAAAAATCCGTTTATTCTACACTGATTTCTCCGGTAAACATTACGGCAAACAAACACTGAC
AACTGCACAAGTTAACGTATCAGCATCAGACAGCTCTTTGAACATCAACGGTGTAGAGGA
TTATAAATCAATCTTTGACGGTGACGGAAAAACGTATCAAAATGTACAGCAGTTCATCGA
TGAAGGCAACTACAGCTCAGGCGACAACCATACGCTGAGAGATCCTCACTACGTAGAAGA
TAAAGGCCACAAATACTTAGTATTTGAAGCAAACACTGGAACTGAAGATGGCTACCAAGG
CGAAGAATCTTTATTTAACAAAGCATACTATGGCAAAAGCACATCATTCTTCCGTCAAGA
AAGTCAAAAACTTCTGCAAAGCGATAAAAAACGCACGGCTGAGTTAGCAAACGGCGCTCT
CGGTATGATTGAGCTAAACGATGATTACACACTGAAAAAAGTGATGAAACCGCTGATTGC
ATCTAACACAGTAACAGATGAAATTGAACGCGCGAACGTCTTTAAAATGAACGGCAAATG
GTACCTGTTCACTGACTCCCGCGGATCAAAAATGACGATTGACGGCATTACGTCTAACGA
TATTTACATGCTTGGTTATGTTTCTAATTCTTTAACTGGCCCATACAAGCCGCTGAACAAA
ACTGGCCTTGTGTTAAAAATGGATCTTGATCCTAACGATGTAACCTTTACTTACTCACACT
TCGCTGTACCTCAAGCGAAAGGAAACAATGTCGTGATTACAAGCTATATGACAAACAGAG
GATTCTACGCAGACAAACAATCAACGTTTGCGCCAAGCTTCCTGCTGAACATCAAAGGCA
AGAAAACATCTGTTGTCAAAGACAGCATCCTTGAACAAGGACAATTAACAGTTAACAAAT
AAAAACGCAAAAGAAAATGCCGATATTGACTACCGGAAGCAGTGTGACCGTGTGCTTCTC
AAATGCCTGATTCAGGCTGTCTATGTGTGACTGTTGAGCTGTAACAAGTTGTCTCAGGTGT
TCAATTTCATGTTCTAGTTGCTTTGTTTTACTGGTTTCACCTGTTCTATTAGGTGTTACATGC
TGTTCATCTGTTACATTGTCGATCTGTTCATGGTGAACAGCTTTAAATGCACCAAAAACTC
GTAAAAGCTCTGATGTATCTATCTTTTTTACACCGTTTTCATCTGTGCATATGGACAGTTTT
CCCTTTGAT (SEQ ID NO: 15)

Δcas3-pro-casA
CAAGACATGTGTATATCACTGTAATTCGATATTTATGAGCAGCATCGAAAAATAGCCCGC
TGATATCATCGATAATACTAAAAAAACAGGGAGGCTATTACCAGGCATCAAATAAAACGA
AAGGCTCAGTCGAAAGACTGGGCCTTTCGTTTTATCTGTTGTTTGTCGGTGAACGCTCTCT
ACTAGAGTCACACTGGCTCACCTTCGGGTGGGCCTTTCTGCGTTTATATCTTTCTGACACCT
TACTATCTTACAAATGTAACAAAAAAGTTATTTTTCTGTAATTCGAGCATGTCATGTTACC
CCGCGAGCATAAAACGCGTGTGTAGGAGGATAATCTTTGACGGCTAGCTCAGTCCTAGGT
ACAGTGCTAGCCATATGAAGGAGAACAAATGAATTTGCTTATTGATAACTGGATCCCTGT
ACGCCCGCGAAACGGGGGGAAAGTCCAAATCATAAATCTGCAATCGCTATAC (SEQ ID NO:
16)

Δcas3::ugBp-sspB-pro-casA
CAAGACATGTGTATATCACTGTAATTCGATATTTATGAGCAGCATCGAAAAATAGCCCGC
TGATATCATCGATAATACTAAAAAAACAGGGAGGCTATTACCAGGCATCAAATAAAACGA
AAGGCTCAGTCGAAAGACTGGGCCTTTCGTTTTATCTGTTGTTTGTCGGTGAACGCTCTCT
ACTAGAGTCACACTGGCTCACCTTCGGGTGGGCCTTTCTGCGTTTATATCTTTCTGACACCT
TACTATCTTACAAATGTAACAAAAAAGTTATTTTTCTGTAATTCGAGCATGTCATGTTACC TABLE 4-continued Synthetic DNA utilized for strain construction.

CCGCGAGCATAAAACGCGTGTGTAGGAGGATAATCTATGGATTTGTCACAGCTAACACCA
CGTCGTCCCTATCTGCTGCGTGCATTCTATGAGTGGTTGCTGGATAACCAGCTCACGCCGC
ACCTGGTGGTGGATGTGACGCTCCCTGGCGTGCAGGTTCCTATGGAATATGCGCGTGACG
GGCAAATCGTACTCAACATTGCGCCGCGTGCTGTCGGCAATCTGGAACTGGCGAATGATG
AGGTGCGCTTTAACGCGCGCTTTGGTGGCATTCCGCGTCAGGTTTCTGTGCCGCTGGCTGC
CGTGCTGGCTATCTACGCCCGTGAAAATGGCGCAGGCACGATGTTTGAGCCTGAAGCTGC
CTACGATGAAGATACCAGCATCATGAATGATGAAGAGGCATCGGCAGACAACGAAACCG
TTATGTCGGTTATTGATGGCGACAAGCCAGATCACGATGATGACACTCATCCTGACGATG
AACCTCCGCAGCCACCACGCGGTGGTCGACCGGCATTACGCGTTGTGAAGTAATTGACGG
CTAGCTCAGTCCTAGGTACAGTGCTAGCCATATGAAGGAGAACAAATGAATTTGCTTATT
GATAACTGGATCCCTGTACGCCCGCGAAACGGGGGAAAGTCCAAATCATAAATCTGCAA
TCGCTATAC (SEQ ID NO: 17)

gltA-DAS + 4-zeoR
GTATTCCGTCTTCCATGTTCACCGTCATTTTCGCAATGGCACGTACCGTTGGCTGGATCGC
CCACTGGAGCGAAATGCACAGTGACGGTATGAAGATTGCCCGTCCGCGTCAGCTGTATAC
AGGATATGAAAAACGCGACTTTAAAAGCGATATCAAGCGTGCGGCCAACGATGAAAACT
ATTCTGAAAACTATGCGGATGCGTCTTAATAGTTGACAATTAATCATCGGCATAGTATATC
GGCATAGTATAATACGACTCACTATAGGAGGGCCATCATGGCCAAGTTGACCAGTGCCGT
TCCGGTGCTCACCGCGCGCGACGTCGCCGGAGCGGTCGAGTTCTGGACCGACCGGCTCGG
GTTCTCCCGGGACTTCGTGGAGGACGACTTCGCCGGTGTGGTCCGGGACGACGTGACCCT
GTTCATCAGCGCGGTCCAGGACCAGGTGGTGCCGGACAACACCCTGGCCTGGGTGTGGGT
GCGCGGCCTGGACGAGCTGTACGCCGAGTGGTCGGAGGTCGTGTCCACGAACTTCCGGGA
CGCCTCCGGGCCGGCCATGACCGAGATCGGCGAGCAGCCGTGGGGGCGGGAGTTCGCCCT
GCGCGACCCGGCCGGCAACTGCGTGCACTTTGTGGCAGAGGAGCAGGACTGAGGATAAG
TAATGGTTGATTGCTAAGTTGTAAATATTTTAACCCGCCGTTCATATGGCGGGTTGATTTTT
ATATGCCTAAACACAAAAAATTGTAAAAATAAAATCCATTAACAGACCTATATAGATATT
TAAAAGAATAGAACAGCTCAAATTATCAGCAACCCAATACTTTCAATTAAAAACTTCAT
GGTAGTCGCATTTATAACCCTATGAAA (SEQ ID NO: 18)

gltA-sfGFP-zeoR
AACGTCGATTTCTACTCTGGTATCATCCTGAAAGCGATGGGTATTCCGTCTTCCATGTTCA
CCGTCATTTTCGCAATGGCACGTACCGTTGGCTGGATCGCCCACTGGAGCGAAATGCACA
GTGACGGTATGAAGATTGCCCGTCCGCGTCAGCTGTATACAGGATATGAAAAACGCGACT
TTAAAAGCGATATCAAGCGTGGGGGTTCAGGCGGGTCGGGTGGCgtgagcaagggcgaggagctgttca
ccggggtggtgcccatcctggtcgagctggacggcgacgtaaacggccacaagttcagcgtgcgcggcgagggcgagggcgatgccaccaac
ggcaagctgaccctgaagttcatctgcaccaccggcaagctgcccgtgccctggcccaccctcgtgaccaccctgacctacggcgtgcagtgcttc
agccgctaccccgaccacatgaagcgccacgacttcttcaagtccgccatgcccgaaggctacgtccaggagcgcaccatcagcttcaaggacga
cggcacctacaagacccgcgccgaggtgaagttcgagggcgacaccctggtgaaccgcatcgagctgaagggcatcgacttcaaggaggacgg
caacatcctggggcacaagctggagtacaacttcaacagccacaacgtctatatcaccgccgacaagcagaagaacggcatcaaggccaacttca
agatccgccacaacgtggaggacggcagcgtgcagctcgccgaccactaccagcagaacacccccatcggcgacggccccgtgctgctgcccg
acaaccactacctgagcacccagtccgtgctgagcaaagaccccaacgagaagcgcgatcacatggtcctgctggagttcgtgaccgccgccgg
gatcactcacggcatggacgagctgtacaagTAATGATGATCGGCACGTAAGAGGTTCCAACTTTCACCATA
ATGAAATAAGATCACTACCGGGCGTATTTTTTGAGTTATCGAGATTTTCAGGAGCTAAGG
AAGCTAAAATGGCTAAACTGACGTCGGCCGTTCCAGTGCTTACTGCGCGTGATGTAGCGG
GAGCCGTAGAGTTTTGGACGGATCGTCTTGGGTTTAGTCGCGACTTTGTGGAAGATGACTT
CGCAGGGGTTGTTCGTGATGACGTCACACTGTTCATCAGTGCCGTACAGGATCAGGTTGTA
CCCGATAACACTCTTGCGTGGGTATGGGTGCGTGGCCTGGATGAGTTATACGCCGAATGG
TCCGAGGTAGTCAGCACAAACTTCCGCGACGCATCCGGGCCCGCTATGACTGAGATCGGG
GAACAACCGTGGGGACGTGAGTTTGCCTTACGTGACCCGGCGGGGAACTGCGTCCACTTT
GTGGCGGAGGAGCAGGACTAAGGATAAGtagTGGTTGATTGCTAAGTTGTAAATATTTTAA
CCCGCCGTTCATATGGCGGGTTGATTTTTATATGCCTAAACACAAAAAATTGTAAAAATAA
AATCCATTAACAGACCTATATAGATATTTAAAAGAATAGAACAGCTCAAATTATCAGCA
ACCCAATACTTTCAATTAAAAACTTCATGGTAGTCGCATTTATAACCCTATGAAAATGACG
TCTATCTATACCCCCCTATATTTTATTCATCATACAACAAATTCATGATACCAATAA (SEQ
ID NO: 19)

gltA-sfGFP-DAS + 4-zeoR
AACGTCGATTTCTACTCTGGTATCATCCTGAAAGCGATGGGTATTCCGTCTTCCATGTTCA
CCGTCATTTTCGCAATGGCACGTACCGTTGGCTGGATCGCCCACTGGAGCGAAATGCACA
GTGACGGTATGAAGATTGCCCGTCCGCGTCAGCTGTATACAGGATATGAAAAACGCGACT
TTAAAAGCGATATCAAGCGTGGGGGTTCAGGCGGGTCGGGTGGCgtgagcaagggcgaggagctgttca
ccggggtggtgcccatcctggtcgagctggacggcgacgtaaacggccacaagttcagcgtgcgcggcgagggcgagggcgatgccaccaac
ggcaagctgaccctgaagttcatctgcaccaccggcaagctgcccgtgccctggcccaccctcgtgaccaccctgacctacggcgtgcagtgcttc
agccgctaccccgaccacatgaagcgccacgacttcttcaagtccgccatgcccgaaggctacgtccaggagcgcaccatcagcttcaaggacga
cggcacctacaagacccgcgccgaggtgaagttcgagggcgacaccctggtgaaccgcatcgagctgaagggcatcgacttcaaggaggacgg
caacatcctggggcacaagctggagtacaacttcaacagccacaacgtctatatcaccgccgacaagcagaagaacggcatcaaggccaacttca
agatccgccacaacgtggaggacggcagcgtgcagctcgccgaccactaccagcagaacacccccatcggcgacggccccgtgctgctgcccg
acaaccactacctgagcacccagtccgtgctgagcaaagaccccaacgagaagcgcgatcacatggtcctgctggagttcgtgaccgccgccgg
gatcactcacggcatggacgagctgtacaagGGTGGGGGTGGGAGCGGCGGCGGTGGCTCCGCGGCCAACG
ATGAAAACTATTCTGAAAACTATGCGGATGCGTCTTAATGATGATCGGCACGTAAGAGGT
TCCAACTTTCACCATAATGAAATAAGATCACTACCGGGCGTATTTTTTGAGTTATCGAGAT
TTTCAGGAGCTAAGGAAGCTAAAATGGCTAAACTGACGTCGGCCGTTCCAGTGCTTACTG
CGCGTGATGTAGCGGGAGCCGTAGAGTTTTGGACGGATCGTCTTGGGTTTAGTCGCGACTT
TGTGGAAGATGACTTCGCAGGGGTTGTTCGTGATGACGTCACACTGTTCATCAGTGCCGTA
CAGGATCAGGTTGTACCCGATAACACTCTTGCGTGGGTATGGGTGCGTGGCCTGGATGAG
TTATACGCCGAATGGTCCGAGGTAGTCAGCACAAACTTCCGCGACGCATCCGGGCCCGCT
ATGACTGAGATCGGGGAACAACCGTGGGGACGTGAGTTTGCCTTACGTGACCCGGCGGGG TABLE 4-continued

| Synthetic DNA utilized for strain construction. |
|---|

AACTGCGTCCACTTTGTGGCGGAGGAGCAGGACTAAGGATAAGtagTGGTTGATTGCTAAG
TTGTAAATATTTTAACCCGCCGTTCATATGGCGGGTTGATTTTTATATGCCTAAACACAAA
AAATTGTAAAAATAAAATCCATTAACAGACCTATATAGATATTTAAAAAGAATAGAACAG
CTCAAATTATCAGCAACCCAATACTTTCAATTAAAAACTTCATGGTAGTCGCATTTATAAC
CCTATGAAAATGACGTCTATCTATACCCCCCTATATTTTATTCATCATACAACAAATTCAT
GATACCAATAA (SEQ ID NO: 20)

zwf-DAS + 4-bsdR
GAAGTGGAAGAAGCCTGGAAATGGGTAGACTCCATTACTGAGGCGTGGGCGATGGACAA
TGATGCGCCGAAACCGTATCAGGCCGGAACCTGGGGACCCGTTGCCTCGGTGGCGATGAT
TACCCGTGATGGTCGTTCCTGGAATGAGTTTGAGGCGGCCAACGATGAAAACTATTCTGA
AAACTATGCGGATGCGTCTTAATAGTTGACAATTAATCATCGGCATAGTATATCGGCATA
GTATAATACGACTCACTATAGGAGGGCCATCATGAAGACCTTCAACATCTCTCAGCAGGA
TCTGGAGCTGGTGGAGGTCGCCACTGAGAAGATCACCATGCTCTATGAGGACAACAAGCA
CCATGTCGGGGCGGCCATCAGGACCAAGACTGGGGAGATCATCTCTGCTGTCCACATTGA
GGCCTACATTGGCAGGGTCACTGTCTGTGCTGAAGCCATTGCCATTGGGTCTGCTGTGAGC
AACGGGCAGAAGGACTTTGACACCATTGTGGCTGTCAGGCACCCCTACTCTGATGAGGTG
GACAGATCCATCAGGGTGGTCAGCCCCTGTGGCATGTGCAGAGAGCTCATCTCTGACTAT
GCTCCTGACTGCTTTGTGCTCATTGAGATGAATGGCAAGCTGGTCAAAACCACCATTGAG
GAACTCATCCCCCTCAAGTACACCAGGAACTAAAGTAATATCTGCGCTTATCCTTTATGGT
TATTTTACCGGTAACATGATCTTGCGCAGATTGTAGAACAATTTTTACACTTTCAGGCCTC
GTGCGGATTCACCCACGAGGCTTTTTTTATTACACTGACTGAAACGTTTTTGCCCTATGAG
CTCCGGTTACAGGCGTTTCAGTCATAAATCCTCTGAATGAAACGCGTTGTGAATC (SEQ ID
NO: 21)

zwf-sfGFP-zeoR
AACGTTTGCTGCTGGAAACCATGCGTGGTATTCAGGCACTGTTTGTACGTCGCGACGAAGT
GGAAGAAGCCTGGAAATGGGTAGACTCCATTACTGAGGCGTGGGCGATGGACAATGATG
CGCCGAAACCGTATCAGGCCGGAACCTGGGGACCCGTTGCCTCGGTGGCGATGATTACCC
GTGATGGTCGTTCCTGGAATGAGTTTGAGGGGGGTTCAGGCGGGTCGGGTGGCgtgagcaaggg
cgaggagctgttcaccggggtggtgcccatcctggtcgagctggacggcgacgtaaacggccacaagttcagcgtgcgcggcgagggcgaggg
cgatgccaccaacggcaagctgaccctgaagttcatctgcaccaccggcaagctgcccgtgccctggcccaccctcgtgaccaccctgacctacg
gcgtgcagtgcttcagccgctaccccgaccacatgaagcgccacgacttcttcaagtccgccatgcccgaaggctacgtccaggagcgcaccatca
gcttcaaggacgacggcacctacaagacccgcgccgaggtgaagttcgagggcgacaccctggtgaaccgcatcgagctgaagggcatcgactt
caaggaggacggcaacatcctggggcacaagctggagtacaacttcaacagccacaacgtctatatcaccgccgacaagcagaagaacggcatc
aaggccaacttcaagatccgccacaacgtggaggacggcagcgtgcagctcgccgaccactaccagcagaacacccccatcggcgacggcccc
gtgctgctgcccgacaaccactacctgagcacccagtccgtgctgagcaaagaccccaacgagaagcgcgatcacatggtcctgctggagttcgtg
accgccgccgggatcactcacggcatggacgagctgtacaagTAATGAATGATCGGCACGTAAGAGGTTCCAACT
TTCACCATAATGAAATAAGATCACTACCGGGCGTATTTTTTGAGTTATCGAGATTTTCAGG
AGCTAAGGAAGCTAAAATGGCCAAGCCTTTGTCTCAAGAAGAATCCACCCTCATTGAAAG
AGCAACGGCTACAATCAACAGCATCCCCATCTCTGAAGACTACAGCGTCGCCAGCGCAGC
TCTCTCTAGCGACGGCCGCATCTTCACTGGTGTCAATGTATATCATTTTACTGGGGGACCT
TGTGCAGAACTCGTGGTGCTGGGCACTGCTGCTGCTGCGGCAGCTGGCAACCTGACTTGT
ATCGTCGCGATCGGAAATGAGAACAGGGGCATCTTGAGCCCCTGCGGACGGTGCCGACAG
GTGCTTCTCGATCTGCATCCTGGGATCAAAGCCATAGTGAAGGACAGTGATGGACAGCCG
ACGGCAGTTGGGATTCGTGAATTGCTGCCCTCTGGTTATGTGTGGGAGGGCTAAGTAGGG
ATAACAGGGTAATTATCTGCGCTTATCCTTTATGGTTATTTTACCGGTAACATGATCTTGC
GCAGATTGTAGAACAATTTTTACACTTTCAGGCCTCGTGCGGATTCACCCACGAGGCTTTT
TTTATTACACTGACTGAAACGTTTTTGCCCTATGAGCTCCGGTTACAGGCGTTTCAGTCAT
AAATCCTCTGAATGAAACGCGTTGTGAATC (SEQ ID NO: 22)

zwf-sfGFP-DAS + 4-zeoR
AACGTTTGCTGCTGGAAACCATGCGTGGTATTCAGGCACTGTTTGTACGTCGCGACGAAGT
GGAAGAAGCCTGGAAATGGGTAGACTCCATTACTGAGGCGTGGGCGATGGACAATGATG
CGCCGAAACCGTATCAGGCCGGAACCTGGGGACCCGTTGCCTCGGTGGCGATGATTACCC
GTGATGGTCGTTCCTGGAATGAGTTTGAGGGGGGTTCAGGCGGGTCGGGTGGCgtgagcaaggg
cgaggagctgttcaccggggtggtgcccatcctggtcgagctggacggcgacgtaaacggccacaagttcagcgtgcgcggcgagggcgaggg
cgatgccaccaacggcaagctgaccctgaagttcatctgcaccaccggcaagctgcccgtgccctggcccaccctcgtgaccaccctgacctacg
gcgtgcagtgcttcagccgctaccccgaccacatgaagcgccacgacttcttcaagtccgccatgcccgaaggctacgtccaggagcgcaccatca
gcttcaaggacgacggcacctacaagacccgcgccgaggtgaagttcgagggcgacaccctggtgaaccgcatcgagctgaagggcatcgactt
caaggaggacggcaacatcctggggcacaagctggagtacaacttcaacagccacaacgtctatatcaccgccgacaagcagaagaacggcatc
aaggccaacttcaagatccgccacaacgtggaggacggcagcgtgcagctcgccgaccactaccagcagaacacccccatcggcgacggcccc
gtgctgctgcccgacaaccactacctgagcacccagtccgtgctgagcaaagaccccaacgagaagcgcgatcacatggtcctgctggagttcgtg
accgccgccgggatcactcacggcatggacgagctgtacaagGGTGGGGGTGGGAGCGGCGGCGGTGGCTCCGC
GGCCAACGATGAAAACTATTCTGAAAACTATGCGGATGCGTCTTAATGAATGATCGGCAC
GTAAGAGGTTCCAACTTTCACCATAATGAAATAAGATCACTACCGGGCGTATTTTTTGAGT
TATCGAGATTTTCAGGAGCTAAGGAAGCTAAAATGGCCAAGCCTTTGTCTCAAGAAGAAT
CCACCCTCATTGAAAGAGCAACGGCTACAATCAACAGCATCCCCATCTCTGAAGACTACA
GCGTCGCCAGCGCAGCTCTCTCTAGCGACGGCCGCATCTTCACTGGTGTCAATGTATATCA
TTTTACTGGGGGACCTTGTGCAGAACTCGTGGTGCTGGGCACTGCTGCTGCTGCGGCAGCT
GGCAACCTGACTTGTATCGTCGCGATCGGAAATGAGAACAGGGGCATCTTGAGCCCCTGC
GGACGGTGCCGACAGGTGCTTCTCGATCTGCATCCTGGGATCAAAGCCATAGTGAAGGAC
AGTGATGGACAGCCGACGGCAGTTGGGATTCGTGAATTGCTGCCCTCTGGTTATGTGTGG
GAGGGCTAAGTAGGGATAACAGGGTAATTATCTGCGCTTATCCTTTATGGTTATTTTACCG
GTAACATGATCTTGCGCAGATTGTAGAACAATTTTTACACTTTCAGGCCTCGTGCGGATTC
ACCCACGAGGCTTTTTTTATTACACTGACTGAAACGTTTTTGCCCTATGAGCTCCGGTTAC
AGGCGTTTCAGTCATAAATCCTCTGAATGAAACGCGTTGTGAATC (SEQ ID NO: 23)

TABLE 4-continued

| Synthetic DNA utilized for strain construction. |
|---|
| lpd-DAS + 4-zeoR<br>GCGGCGAGCTGCTGGGTGAAATCGGCCTGGCAATCGAAATGGGTTGTGATGCTGAAGACA<br>TCGCACTGACCATCCACGCGCACCCGACTCTGCACGAGTCTGTGGGCCTGGCGGCAGAAG<br>TGTTCGAAGGTAGCATTACCGACCTGCCGAACCCGAAAGCGAAGAAGAAGGCGGCCAAC<br>GATGAAAACTATTCTGAAAACTATGCGGATGCGTCTTAATAGCGAATCCATGTGGGAGTT<br>TATTCTTGACACAGATATTTATGATATAATAACTGAGTAAGCTTAACATAAGGAGGAAAA<br>ACATATGTTACGCAGCAGCAACGATGTTACGCAGCAGGGCAGTCGCCCTAAAACAAAGTT<br>AGGTGGCTCAAGTATGGGCATCATTCGCACATGTAGGCTCGGCCCTGACCAAGTCAAATC<br>CATGCGGGCTGCTCTTGATCTTTTCGGTCGTGAGTTCGGAGACGTAGCCACCTACTCCCAA<br>CATCAGCCGGACTCCGATTACCTCGGGAACTTGCTCCGTAGTAAGACATTCATCGCGCTTG<br>CTGCCTTCGACCAAGAAGCGGTTGTTGGCGCTCTCGCGGCTTACGTTCTGCCCAAGTTTGA<br>GCAGCCGCGTAGTGAGATCTATATCTATGATCTCGCAGTCTCCGGCGAGCACCGGAGGCA<br>GGGCATTGCCACCGCGCTCATCAATCTCCTCAAGCATGAGGCCAACGCGCTTGGTGCTTAT<br>GTGATCTACGTGCAAGCAGATTACGGTGACGATCCCGCAGTGGCTCTCTATACAAAGTTG<br>GGCATACGGGAAGAAGTGATGCACTTTGATATCGACCCAAGTACCGCCACCTAATTTTTC<br>GTTTGCCGGAACATCCGGCAATTAAAAAAGCGGCTAACCACGCCGCTTTTTTTACGTCTGC<br>AATTTACCTTTCCAGTCTTCTTGCTCCACGTTCAGAGAGACGTTCGCATACTGCTGACCGTT<br>GCTCGTTATTCAGCCTGACAGTATGGTTACTGTC (SEQ ID NO: 24) |

Strains & Plasmids

Plasmid and strain information are found in Tables 2-4. Sequences of oligonucleotides and synthetic linear DNA (Gblocks™) were obtained from Integrated DNA Technologies (IDT, Coralville, IA). Deletions were constructed with tet-sacB based selection and counterselection. C-terminal DAS+4 tag (with or without superfolder GFP tags) were added to chromosomal genes by direct integration and selected through integration of antibiotic resistance cassettes 3' of the gene. All strains were confirmed by PCR, agarose gel electrophoresis and confirmed by sequencing (Eton Biosciences, or Genewiz) using paired oligonucleotides, either flanking the entire region. The recombineering plasmid pSIM5 and the tet-sacB selection/counterselection marker cassette were kind gifts from Donald Court (NCI, redrecombineering.ncifcrf.gov/court-lab.html). Strain BW25113 was obtained from the Yale Genetic Stock Center (CGSC: cgsc.biology.yale.edu). Strain DLF_R002 was constructed as previously reported by Menacho-Melgar et al. (doi: 10.1101/820787). Strain DLFZ_0025 was constructed from DLF_R002 by first deleting the native sspB gene (using tet-sacB based selection and counterselection). Subsequently, the cas3 gene was deleted and replaced with a low phosphate inducible sspB (using the ugpB gene promoter) allele as well as a constitutive promoter to drive expression of the Cascade operon (again using tet-sacB based selection and counterselection). C-terminal DAS+4 tag modifications (with or without superfolder GFP tags) were added to the chromosome of DLF_Z0025 and its derivatives by direct integration and selected through integration of antibiotic resistance cassettes 3' of the gene.

Plasmids, pCDF-ev (Addgene #89596), pHCKan-yibDp-GFPuv (Addgene #127078) and pHCKan-yibDp-cimA3.7 (Addgene #134595) were constructed as previously reported (doi: 10.1101/820787). Plasmids pCDF-mCherry1 (Addgene #87144) and pCDF-mCherry1 (Addgene #87145) were constructed from pCDF-ev by PCR and Gibson assembly with synthetic DNA encoding an mCherry open reading frame with out without a C-terminal DAS+4 degron tag along with a strong synthetic constitutive proD promoter previously reported by Davis et al.

Gene silencing guides and guide arrays were expressed from a series of pCASCADE plasmids. The pCASCADE-control plasmid was prepared by swapping the pTet promoter in perRNA.Tet (a kind gift from C. Beisel) with an insulated low phosphate induced ugpB promoter. In order to design CASCADE guide array, CASCADE PAM sites near the −35 or −10 box of the promoter of interest were identified, 30 bp at the 3' end of PAM site was selected as the guide sequence and cloned into pCASCADE plasmid using Q5 site-directed mutagenesis (NEB, MA) following manufacturer's protocol, with the modification that 5% v/v DMSO was added to the Q5 PCR reaction. PCR cycles were as follows: amplification involved an initial denaturation step at 98° C. for 30 second followed by cycling at 98° C. for 10 second, 72° C. for 30 second, and 72° C. for 1.5 min (the extension rate was 30 second/kb) for 25 cycles, then a final extension for 2 min at 72° C. 2 μL of PCR mixture was used for 10 μL, KLD reaction (NEB, MA), which proceeded under room temperature for 1 hour, after which, 1 μL KLD mixture was used for electroporation. The pCASCADE guide array plasmid (pCASCADE-G2Z) was prepared by sequentially amplifying complementary halves of each smaller guide plasmid by PCR, followed by subsequent DNA assembly as illustrated in Tables. Primers used for pCASCADE assembly and gRNA sequences are provided in Supplemental Table 5 below. Additionally, all strains containing gRNA plasmids were routinely confirmed to assess gRNA stability via PCR as described below.

TABLE 5

List of sgRNA guide sequences and primers used to construct them. Spacers are italicized.

| sgRNA/Primer Name | Sequence | Template |
|---|---|---|
| gltA2 | *TCGAGTTCCCCGCGCCAGCGGGGATAAACCG*TATTGACCAA<br>TTCATTCGGGACAGTTATTAGT*TCGAGTTCCCCGCGCCAGC*<br>*GGGGATAAACCG* (SEQ ID NO: 27) | |

TABLE 5-continued

List of sgRNA guide sequences and primers used to construct them. Spacers are italicized.

| sgRNA/Primer Name | Sequence | Template |
|---|---|---|
| gltA2-FOR | GGGACAGTTATTAGTTCGAGTTCCCCGCGCCAGCGGGGATAAACCGAAAAAAAAAACCCC (SEQ ID NO: 28) | pCASCADE ev |
| gltA2-REV | GAATGAATTGGTCAATACGGTTTATCCCCGCTGGCGCGGGGAACTCGAGGTGGTACCAGATCT (SEQ ID NO: 29) | |
| proD | *TCGAGTTCCCCGCGCCAGCGGGGATAAACCG*AGTGGTTGCTGGATAACTTTACGGGCATGC*TCGAGTTCCCCGCGCCAGCGGGGATAAACCG* (SEQ ID NO: 30) | |
| proD-FOR | AACTTTACGGGCATGCTCGAGTTCCCCGCGCCAGCGGGGATAAACCGAAAAAAAAAACCCC (SEQ ID NO: 31) | pCASCADE ev |
| proD-REV | ATCCAGCAACCACTCGGTTTATCCCCGCTGGCGCGGGGAACTCGAGGTGGTACCAGATCT (SEQ ID NO: 32) | |
| zwf | *TCGAGTTCCCCGCGCCAGCGGGGATAAACCG*CTCGTAAAAGCAGTACAGTGCACCGTAAGA*TCGAGTTCCCCGCGCCAGCGGGGATAAACCG* (SEQ ID NO: 33) | |
| zwf-FOR | CAGTGCACCGTAAGATCGAGTTCCCCGCGCCAGCGGGGATAAACCGAAAAAAAAAACCCC (SEQ ID NO: 34) | pCASCADE ev |
| zwf-REV | TACTGCTTTTACGAGCGGTTTATCCCCGCTGGCGCGGGGAACTCGAGGTGGTACCAGATC (SEQ ID NO: 35) | |
| G2Z | *TCGAGTTCCCCGCGCCAGCGGGGATAAACCGTATTGACCAATTCATTC*GGGACAGTTATTAGT*TCGAGTTCCCCGCGCCAGCGGGGATAAACCG*CTCGTAAAAGCAGTACAGTGCACCGTAAGA*TCGAGTTCCCCGCGCCAGCGGGGATAAACCG* (SEQ ID NO: 36) | |
| zwf-FOR | GCGCCAGCGGGGATAAACCGCTCGTAAAAG (SEQ ID NO: 37) | pCASCADE-zwf |
| pCASCADE-REV | CTTGCCCGCCTGATGAATGCTCATCCGG (SEQ ID NO: 38) | |
| pCASCADE-FOR | CCGGATGAGCATTCATCAGGCGGGCAAG (SEQ ID NO: 39) | pCASCADE-G2 |
| gltA2-REV | CGGTTTATCCCCGCTGGCGCGGGGAACTCGAACTAATAACTGTC (SEQ ID NO: 40) | |

BioLector Studies

Single colonies of each strain were inoculated into 5 mL LB with appropriate antibiotics and cultured at 37° C., 220 rpm for 9 hours or until OD600 reached >2. 500 μL of the culture was inoculated into 10 mL SM10 medium with appropriate antibiotics, and cultured in a square shake flask (CAT #: 25-212, Genesee Scientific, Inc. San Diego, CA) at 37° C., 220 rpm for 16 hours. Cells were pelleted by centrifugation and the culture density was normalized to OD600=5 using FGM3 media. Growth and fluorescence measurements were obtained in a Biolector (m2p labs, Baesweiler, Germany) using a high mass transfer Flower-Plate (CAT #: MTP-48-B, m2p-labs, Germany). 40 μL of the OD normalized culture was inoculated into 760 μL of FGM3 medium with appropriate antibiotics. Biolector settings were as follows: RFP gain=100, GFP gain=20, Biomass gain=20, shaking speed=1300 rpm, temperature=37° C., humidity=85%. Every strain was analyzed in triplicate.

ELISAs

Quantification of proteins via C-terminal GFP tags was performed using a GFP quantification kit from AbCam (Cambridge, UK, product #ab171581) according to manufacturer's instructions. Briefly, samples were obtained from microfermentations as described above. Cells were harvested 24 hour post phosphate depletion, washed in water and lysed with the provided extraction buffer.

Guide RNA Stability Testing

The stability of guide RNA arrays was confirmed by colony PCR using the following 2 primers: gRNA-for: 5'-GGGAGACCACAACGG-3' (SEQ ID NO: 25), gRNA-rev: 5'-CGCAGTCGAACGACCG-3' (SEQ ID NO: 26), using 2× EconoTaq Master mix (Lucigen) in 10 μL, PCR reactions consisting of 5 μL of 2× EconoTaq Master mix (Lucigen), 1 uL of each primer (10 μM), 3 μL dH2O. A 98° C., 2 minute initial denaturation was followed by 35 cycles of 94° C., 30 seconds, 60° C. 30 seconds, and 72° C., 30 seconds and a final 72° C., 5 min final extension. PCR reactions were then run on agarose gels and band size compared to control PCR reactions using purified plasmid DNA as a template. Guide protospacer loss occurred when guide array size was smaller than expected, indicating the loss of one or more protospacers.

Fermentations

Minimal media microfermentations were performed as previously reported (doi: 10.1021/acssynbio.0c00182). For microfermentations where paraquat induction was used, paraquat was added for 1 hour prior to phosphate depletion and subsequently removed during the cell wash step used to deplete phosphate in the media. 1 L fermentations in instrumented bioreactors were also performed as previously reported, with slight modifications to the glucose feeding profiles, which were a function of strain and process. Generally, feeding was increased to enable excess residual glucose to ensure production rates were not feed limited.

Glucose feeding was as follows. For 10 gCDW/L fermentations, starting batch glucose concentration was 25 g/L. A constant concentrated sterile filtered glucose feed (500 g/L) was added to the tanks at 1.5 g/h when cells entered mid-exponential growth. For 25 gCDW/L fermentations, starting batch glucose concentration was 25 g/L. Concentrated sterile filtered glucose feed (500 g/L) was added to the tanks at an initial rate of 9 g/h when cells entered mid-exponential growth. This rate was then increased exponentially, doubling every 1.083 hours (65 min) until 40 g total glucose had been added, after which the feed was maintained at 1.75 g/hr.

Production of Isotopically Labelled Metabolites.

$C^{13}$ pyruvate (CLM-1082-PK) and $C^{13}$ D-glucose (U-13C6, 99%) were purchased from Cambridge Isotope Laboratories, Inc. (Tewksbury, MA). Isotopically labelled citramalate was produced in two stage minimal media shake flask studies, mimicking microfermentations, using strain DLF_Z0044 expressing cimA3.7. Briefly, 20 mL cultures of SM10++ media were inoculated with the strain which was grown overnight at 37 Celsius, shaking at 150 rpm in baffled 250 mL Erlenmyer shake flasks. After 16 hrs of growth cells were harvested by centrifugation washed and resuspended in 20 mL of SM10 minimal media (lacking phosphate) where glucose was replaced with $C^{13}$ labelled glucose. Cultures were grown for 25 hrs at 37 Celsius, shaking at 150 rpm, after which cells were removed by centrifugation, and the spent media filter sterilized prior to use as an internal standard.

Analytical Methods

Cell dry weights: The OD/cell dry weight correlation coefficient (1 OD (600 nm)=0.35 gCDW/L, as determined by Menacho-Melgar et al. was used in this work.

Glucose and Organic Acid Quantification: Two methods were used for glucose and organic acid quantification. First, a UPLC-RI method was developed for the simultaneous quantification of glucose, citramalate, acetic acid, pyruvate, citraconate, citrate and other organic acids including lactate, succinate, fumarate, malate, and mevalonate. Chromatographic separation was performed using a Rezex Fast Acid Analysis HPLC Column (100×7.8 mm, 9 μm particle size; CAT #: #1250100, Bio-Rad Laboratories, Inc., Hercules, CA) at 55° C. 5 mM sulfuric acid was used as the isocratic eluent, with a flow rate of XmL/min. Sample injection volume was 10 μL. Second, quantification was performed using a Bio-Rad Fast Acid Analysis HPLC Column (100×7.8 mm, 9 μm particle size; CAT #: #1250100, Bio-Rad Laboratories, Inc., Hercules, CA) at 65° C. 10 mM sulfuric acid was used as the eluent, with an isocratic flow rate of 0.3 mL/min. In both methods, sample injection volume was 10 μL and chromatography and detection were accomplished using a Waters Acquity H-Class UPLC integrated with a Waters 2414 Refractive Index (RI) detector (Waters Corp., Milford, MA USA). Samples were diluted as needed to be within the accurate linear range. Dilution was performed using ultrapure water.

Organic acid Quantification via RapidFire-qTOE-MS: Micro-fermentation samples (as well as a confirmatory subset of samples from bioreactors) were centrifuged to remove cells. Broth was diluted 100 fold in water to a final volume of 20 μL. To this either a final concentration of 10 mg/L of C13 pyruvate was added or 2 uL of broth containing C13 labelled citramalate was added. The final sample was injected onto a HILIC (type H1 or the equivalent H6) RapidFire™ cartridge (Agilent Technologies, Santa Clara, CA). Injections were loaded on the cartridge with 95% hexane, 5% isopropanol for 3000 ms after a 600 ms aspiration, at a flow rate of 1.0 mL/min. After loading, the cartridge was washed with isopropanol for 2000 ms, at a flow rate of 1.0 mL/min. Elution was carried out for 8000 ms with 50% water/50% methanol with 0.2% acetic acid and 0.5 uM $(NH_4)_3PO_4$, at a flow rate of 1.0 mL/min. Column equilibration was performed for 4000 ms. The qTOF was tuned in the mass range of 50-250 m/z in fragile ion, negative ESI mode. Settings during detection were as follows: drying gas: 250 C at a flow rate of 13 L/minute, sheath gas: 400 C at a flow rate of 12 L/minute, nebulizer pressure: 35 psi, Fragmenter voltage: 100 V, skimmer voltage: 65 V, nozzle voltage: 2000 V, capillary voltage: 3500V. The acquisition rate was 1 spectra/second.

Figure 2A:
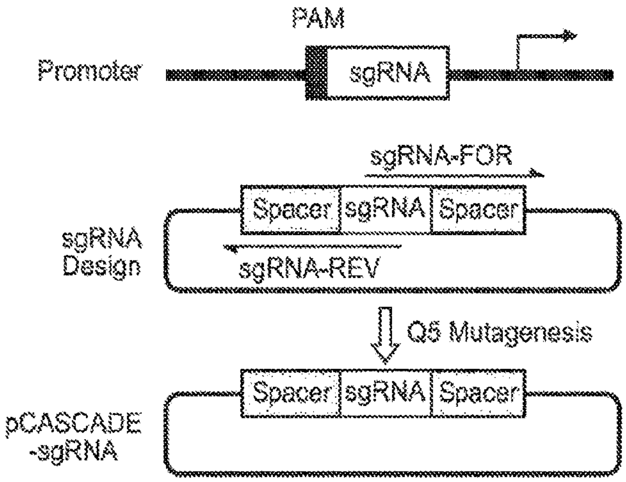
FIG. 2 depicts pCASCADE construction scheme. (2A) single sgRNA cloning; (2B) double sgRNA.
Figure 2B:
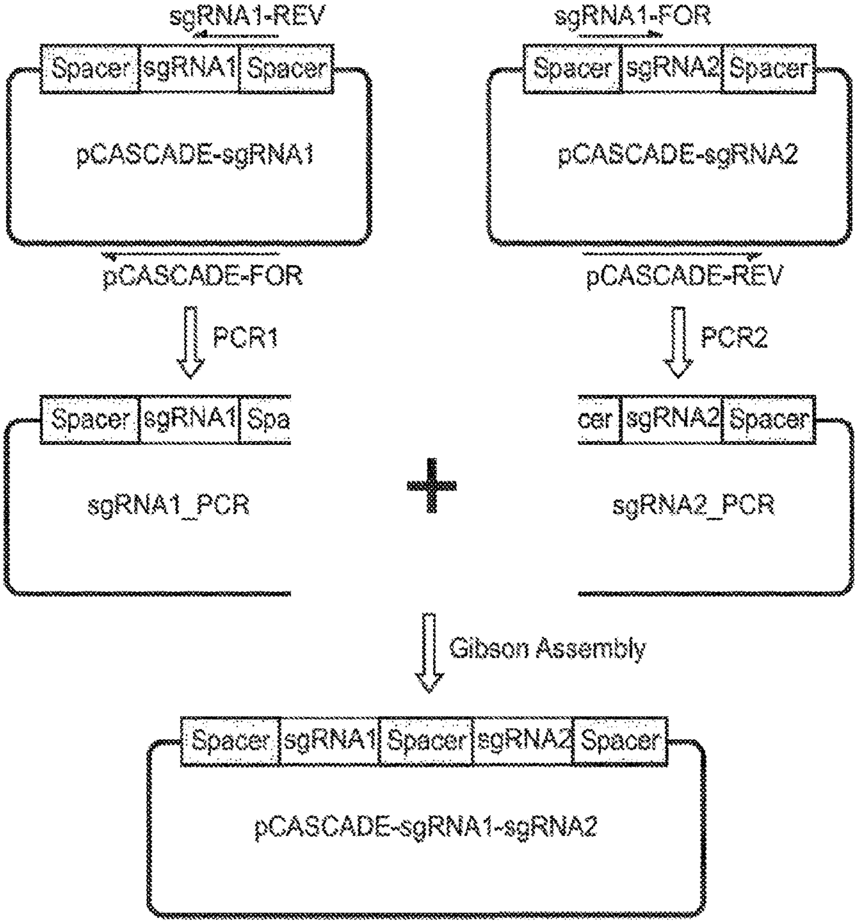

Example 1: Gene Silencing Arrays & Pathway Expression Constructs pCASCADE Guide Array based Gene Silencing The design and construction of CASCADE guides and guide arrays is illustrated below in FIG. 1 and FIG. 2. The pCASCADE-control plasmid was prepared by swapping the pTet promoter in perRNA.Tet with an insulated low phosphate induced ugpB promoter, as illustrated in FIG. 1. Two promoters were responsible for regulating gltA gene, and sgRNA was designed for both promoters. Four promoters were responsible for regulating gapA gene, and sgRNA was designed for the first promoter, since during exponential phase of growth, gapA mRNAs were mainly initiated at the highly efficient gapA P1 promoter and remained high during stationary phase compared to the other three gapA promoters. Multiple promoters upstream of lpd gene were involved in lpd regulation (ecocyc.org/gene?orgid=ECOLI&id=EG10543#tab=showAll), thus design of unique and effective sgRNA for lpd only was not possible. Promoter sequences for fabI, udhA and zwf were obtained from EcoCyc database (ecocyc.org). In order to design CASCADE guide array, CASCADE PAM sites near the −35 or −10 box of the promoter of interest were identified, 30 bp at the 3' end of PAM site was selected as the guide sequence and cloned into pCASCADE plasmid using Q5 site-directed mutagenesis (NEB, MA) following manufacturer's protocol, with the modification that 5% v/v DMSO was added to the Q5 PCR reaction. The pCASCADE-control vector was used as template. pCASCADE plasmids with arrays of two or more guides were prepared as described below and illustrated in FIG. 2. The pCASCADE guide array plasmid was prepared by sequentially amplifying complementary halves of each smaller guide plasmid by PCR, followed by subsequent DNA assembly. Table 6 and 7 lists sgRNA guide sequences and primers used to construct them. All pCASCADE silencing plasmids are listed in Tables below and are available at Addgene.

TABLE 6

| List of sgRNA guide sequences and primers used to construct them. Spacers are italicized. | | |
|---|---|---|
| sgRNA/Primer Name | Sequence | Template |
| gltA2 | *TCGAGTTCCCCGCGCCAGCGGGGATAAACCG*TATTGACCAATTCATTCGGGACAGTTATTAGT*TCGAGTTCCCCGCGCCAGCGGGGATAAACCG* (SEQ ID NO: 27) | |
| gltA2-FOR | GGGACAGTTATTAGTTCGAGTTCCCCGCGCCAGCGGGGATAAACCGAAAAAAAAAACCCC (SEQ ID NO: 28) | pCASCADE ev |
| gltA2-REV | GAATGAATTGGTCAATACGGTTTATCCCCGCTGGCGCGGGGAACTCGAGGTGGTACCAGATCT (SEQ ID NO: 29) | |
| proD | *TCGAGTTCCCCGCGCCAGCGGGGATAAACCG*AGTGGTTGCTGGATAACTTTACGGGCATGC*TCGAGTTCCCCGCGCCAGCGGGGATAAACCG* (SEQ ID NO: 30) | |
| proD-FOR | AACTTTACGGGCATGCTCGAGTTCCCCGCGCCAGCGGGGATAAACCGAAAAAAAAAACCCC (SEQ ID NO: 31) | pCASCADE ev |
| proD-REV | ATCCAGCAACCACTCGGTTTATCCCCGCTGGCGCGGGGAACTCGAGGTGGTACCAGATCT (SEQ ID NO: 32) | |
| zwf | *TCGAGTTCCCCGCGCCAGCGGGGATAAACCG*CTCGTAAAAGCAGTACAGTGCACCGTAAGA*TCGAGTTCCCCGCGCCAGCGGGGATAAACCG* (SEQ ID NO: 33) | |
| zwf-FOR | CAGTGCACCGTAAGATCGAGTTCCCCGCGCCAGCGGGGATAAACCGAAAAAAAAAACCCC (SEQ ID NO: 34) | pCASCADE ev |
| zwf-REV | TACTGCTTTTACGAGCGGTTTATCCCCGCTGGCGCGGGGAACTCGAGGTGGTACCAGATC (SEQ ID NO: 35) | |
| G2Z | *TCGAGTTCCCCGCGCCAGCGGGGATAAACCGTATTGACCAATTCATTC*GGGACAGTTATTAGT*TCGAGTTCCCCGCGCCAGCGGGGATAAACCG*CTCGTAAAAGCAGTACAGTGCACCGTAAGA*TCGAGTTCCCCGCGCCAGCGGGGATAAACCG* (SEQ ID NO: 36) | |
| zwf-FOR | GCGCCAGCGGGGATAAACCGCTCGTAAAAG (SEQ ID NO: 37) | pCASCADE-zwf |
| pCASCADE-REV | CTTGCCCGCCTGATGAATGCTCATCCGG (SEQ ID NO: 38) | |
| pCASCADE-FOR | CCGGATGAGCATTCATCAGGCGGGCAAG (SEQ ID NO: 39) | pCASCADE-G2 |
| gltA2-REV | CGGTTTATCCCCGCTGGCGCGGGGAACTCGAACTAATAACTGTC (SEQ ID NO: 40) | |

TABLE 7

| List of plasmids used in this study. | | | | | |
|---|---|---|---|---|---|
| Plasmid | Insert | Origin | Res | Addgene ID | Source |
| Plasmid Utilized in this Study | | | | | |
| pSIM5 | Recombineering genes | pSC101ts | Cm | NA | Court Lab |
| pSMART-HC-Kan | None - empty vector (ev) | ColE1 | Kan | NA | Lucigen |
| pcrRNA.Tet | gRNA control template | p15a | Cm | NA | Beisel Lab[2] |
| pCDF-ev | none control template | CloDF13 | Sp | 89596 | [1] |
| pSMART-GFPuv | yibDp-GFPuv | ColE1 | Kan | 65822 | [1] |
| pHCKan-yibDp-cimA3.7 | yibDp-cimA3.7 | ColE1 | Kan | 134595 | [1] |
| Plasmid Constructed in this Study | | | | | |
| pCDF-mcherry1 | proDp-mCherry | CloDF13 | Sp | 87144 | this study |
| pCDF-mcherry2 | proDp-mCherry-DAS + 4 | CloDF13 | Sp | 87145 | this study |
| pCASCADE-ev | empty gRNA control | p15a | Cm | 65821 | this study |
| pCASCADE-proD | proDp silencing gRNA | p15a | Cm | 65820 | this study |
| pCASCADE-F | fabIp silencing gRNA | p15a | Cm | 66635 | this study |

TABLE 7-continued

| List of plasmids used in this study. | | | | | |
|---|---|---|---|---|---|
| Plasmid | Insert | Origin | Res | Addgene ID | Source |
| pCASCADE-G2 | gltA2p silencing gRNA | p15a | Cm | 65817 | this study |
| pCASCADE-Z | zwfp silencing gRNA | p15a | Cm | 65825 | this study |
| pCASCADE-G2Z | gltA2p, zwfp silencing gRNA array | p15a | Cm | 71338 | this study |

Example 2: Dynamic Control Over Protein Levels

Plasmids expressing fluorescent proteins and silencing guides were transformed into the corresponding hosts strain listed in Table 2. Strains were evaluated in triplicate in an m2p-labs Biolector™, which simultaneously measures fluorescence including GFPuv and mCherry levels, as well as biomass levels. Results are given in FIG. 5.

TABLE 8

| Strains used for Dynamic Control over protein levels | | |
|---|---|---|
| RFP Strain | Plasmid | Host Strain |
| mCherry-control | pCDF-mcherry1 | DLF_Z002 |
| Proteolysis | pCDF-mcherry2 | DLF_Z0025 |
| Silencing | pCDF-mcherry1 + pCASCADE-proD | DLF_Z01517 |
| Proteolysis + Silencing | pCDF-mcherry2 + pCASCADE-proD | DLF_Z0025 |

OD600 readings were corrected using the formula below, where OD600 refers to an offline measurement, OD600* refers to Biolector biomass reading, $t_0$ indicates the start point, and tf indicates the final point.

Equation S1

$$OD600_t = (OD600^*_t - OD600^*_{t0})*\frac{(OD600_{tf} - OD600_{to})}{(OD600^*_{tf} - OD600^*_{to})} + 0.25$$

Figure 3A:
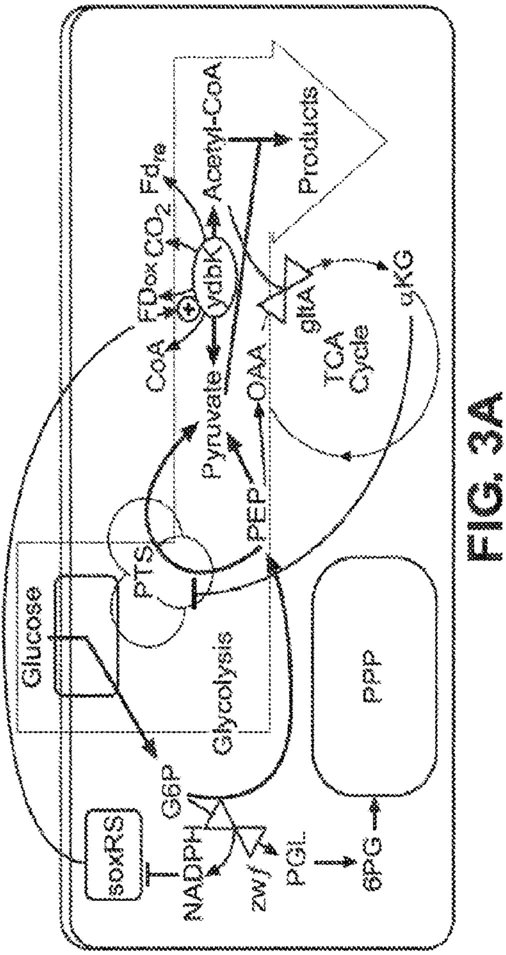
FIG. 3A-I: (A) A schematic of two-stage dynamic control over feedback regulation of central metabolism improves stationary phase sugar uptake and acetyl-CoA flux. Metabolic valves (double triangles) dynamically reduce levels off Zwf (glucose-6-phosphate dehydrogenase) and GltA (citrate synthase). Reduced flux through the TCA cycle reduces αKG levels alleviating feedback inhibition of PTS dependent glucose uptake, improving glycolytic fluxes and pyruvate production. Reduced flux Zwf reduces NADPH levels activating the SoxRS oxidative stress response regulation and increasing expression and activity of pyruvate ferredoxin oxidoreductase improving pyruvate oxidation and acetyl-CoA flux. (b) Time course of two stage dynamic metabolic control upon phosphate depletion Biomass levels accumulate and consume a limiting nutrient (in this case inorganic phosphate), which when depleted triggers entry into a productive stationary phase, levels of key enzymes are dynamically reduced with synthetic metabolic valves (red) (c & d). Synthetic metabolic valves utilizing CRISPRi based gene silencing and/or controlled proteolysis. (c) Array of silencing guides can be used to silencing target multiple genes of interest (GOI). This involves the inducible expression of one or many guide RNAs as well as expression of the modified native Cascade system wherein the cas3 nuclease is deleted. The gRNA/Cascade complex binds to target sequences in the promoter region and silences transcription. (d) C-terminal DAS+4 tags are added to enzymes of interest (EOI) through chromosomal modification, they can be inducibly degraded by the clpXP protease in the presence of an inducible sspB chaperone. (e) Dynamic control over protein levels in *E. coli* using inducible proteolysis and CRISPRi silencing. As cells grow phosphate is depleted, cells "turn off" mCherry and "turn on" GFPuv. Shaded areas represent one standard deviation from the mean, n=3. (f) The relative impact of proteolysis and gene silencing alone and in combination on mCherry degradation, (g) mCherry decays rates. (h & i) Dynamic Control over the levels of the central metabolic enzymes. The impact of silencing (pCASCADE) and proteolysis (DAS+4 tags) on protein levels were evaluated alone and in combination (h) GltA (citrate synthase), and (i) Zwf (glucose-6-phosphate dehydrogenase). In all cases chromosomal genes were tagged with a C-terminal sfGFP. Protein levels were measured by ELISA, 24 hour post induction by phosphate depletion in microfermentations. Abbreviations: PTS: phosphotransferase transport system, PPP: pentose phosphate pathway, TCA: tricarboxylic acid, G6P: glucose-6-phosphate, 6-PGL: 6-phosphogluconolactone, 6PG: 6-phosphogluconate, PEP: phosphoenolpyruvate, Fd: ferredoxin, CoA: coenzyme A, OAA: oxaloacetate, αKG: α-ketoglutarate.

Example 3: Impact of Dynamic Control of Two Central Metabolic Pathways TCA and PPP on Flux Through Glycolysis and Pyruvate Oxidation As illustrated in FIG. 3A, the impact of dynamic control of two central metabolic pathways (the tricarboxylic acid (TCA) cycle and pentose phosphate pathway (PPP)) on flux through glycolysis and pyruvate oxidation are desired. We accomplish this by creating synthetic metabolic valves, to dynamically reduce levels of the first committed step in each pathway, namely citrate synthase (GltA, "G", encoded by the gltA gene) and glucose 6-phosphate dehydrogenase (Zwf, "Z", encoded by the zwf gene). We show that dynamic control over these two enzymes improves stationary phase production of pyruvate, and citramalate, and have applicability in the production of numerous products requiring pyruvate and/or acetyl-CoA.

Figure 3B:
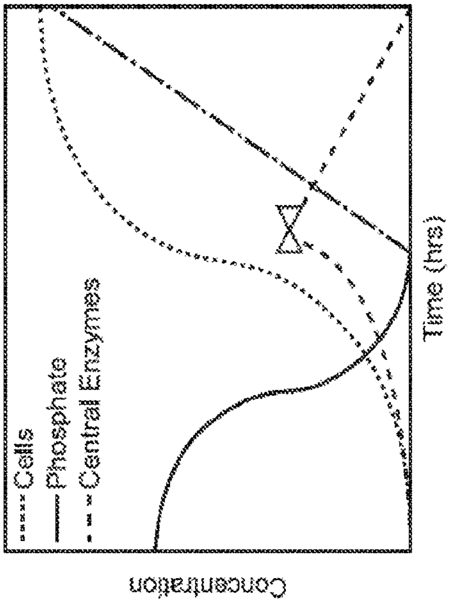
Figure 3C:
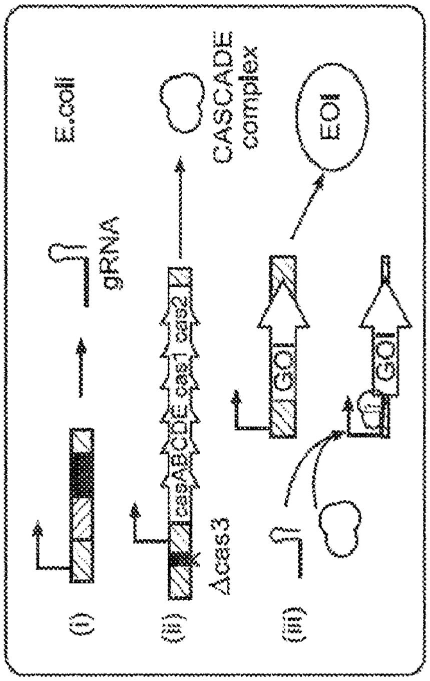
Figure 3D:
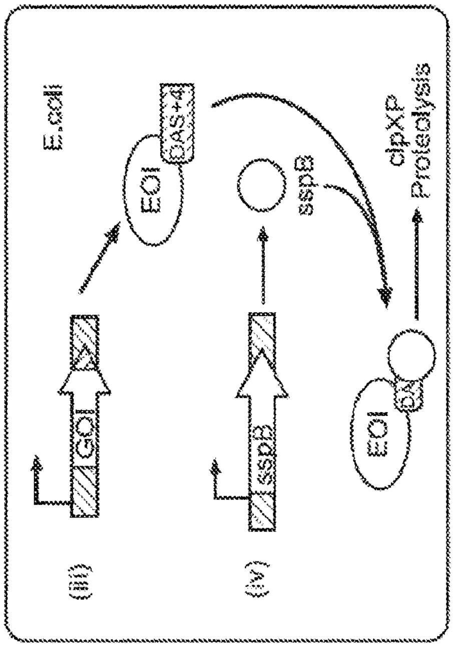
Figure 3E:
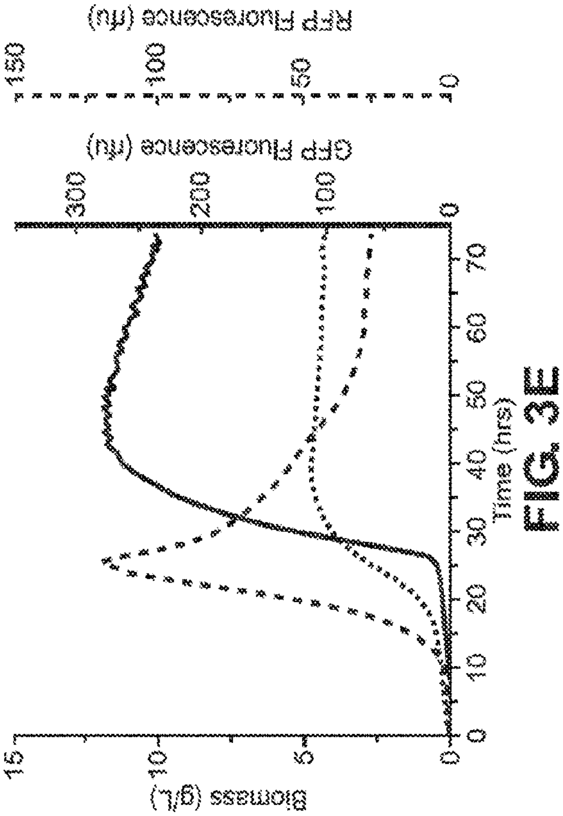
Figure 3F:
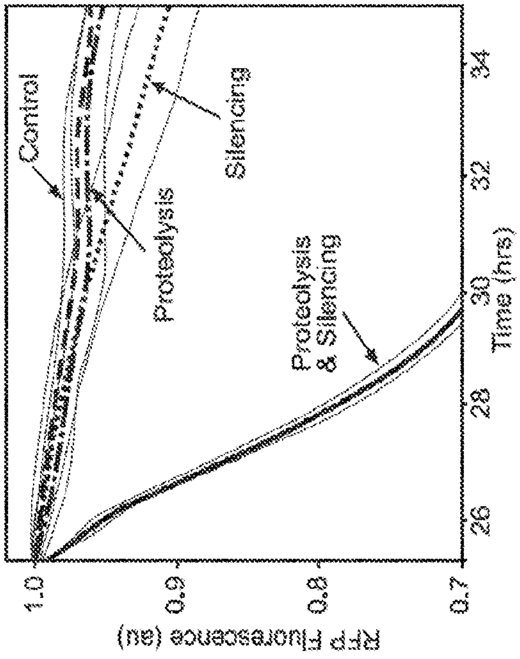
Figure 3G:
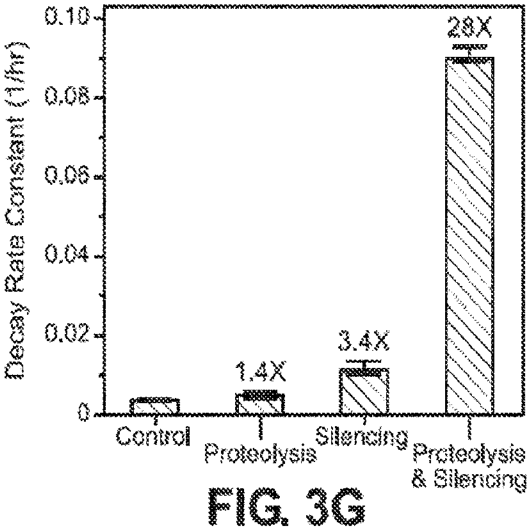

We first developed control systems capable of the dynamic reduction of protein levels in two-stage processes, as illustrated in FIG. 3B-D. Valves may include controlled proteolysis or CRISPRi/Cascade based gene silencing or both proteolysis and silencing in combination to reduce levels of key metabolic enzymes. Induction is implemented using phosphate depletion as an environmental trigger. The native *E. coli* Type I-E Cascade/CRISPR system is used for gene silencing (FIG. 3Ci-iii). Targeted proteolysis is implemented by linking the expression of the chaperone SspB to phosphate deprivation. SspB, when induced, binds to C-terminal DAS+4 peptide tags on any target protein and causes degradation by the ClpXP protease of *E. coli* (FIG. 3D). Using engineered strains, as FIG. 1E demonstrates, protein levels can be controlled in a two-stage process, as exemplified by turning "ON" GFP and "OFF" constitutively expressed mCherry. While, in this case, the combination of gene silencing with proteolysis results in the largest rates of protein degradation (FIG. 3F-G), the impact of each approach and specific decay rates, will vary depending on the target gene/enzyme and its specific natural turnover rates and expression levels.

Figure 3H:
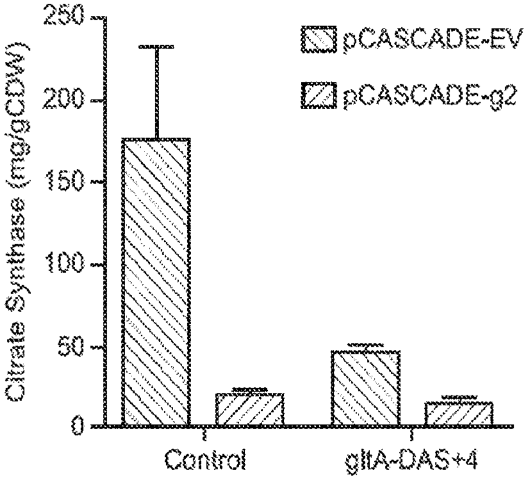
Figure 3I:
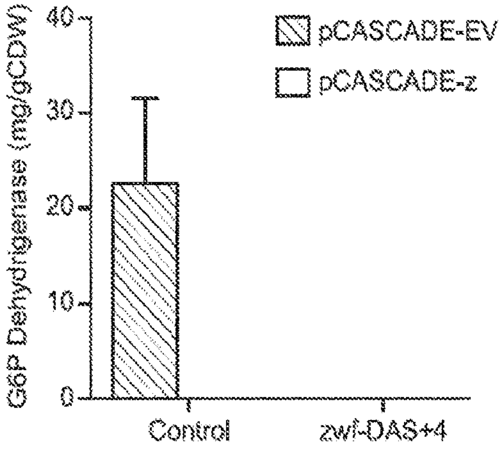

In order to dynamically reduce levels of GltA and Zwf (FIG. 3H-I), strains were engineered with chromosomal modifications that appended C-terminal DAS+4 degron tags to these genes. In addition, we engineered several strains to have C-terminal superfolder GFP tags behind each gene with and without C-terminal degron tags. Plasmids expressing gRNAs were designed to repress expression from the gltAp2 and zwf promoters. Using these strains and plasmids, dynamic control over enzyme levels were monitored by tracking GFP via an ELISA assay in two-stage minimal media micro-fermentations as reported by Moreb et al. An ELISA was used as protein levels were too low in engineered strains to use GFP fluorescence as a direct reporter. In the case of GltA proteolysis and silencing resulted in a 70% and 85% decrease in GltA levels, respectively, with the combination resulting in a 90% reduction. In the case of Zwf, proteolysis, silencing as well as the combination all resulted in protein levels below the limit of quantification of our assay.

The impact of "G" and "Z" valve combinations on metabolic fluxes were measured in minimal media micro-fermentations, performed without any heterologous production pathway. As the strains used had deletions in the major pathways leading to acetate production (poxB, and pta-ackA), pyruvate synthesis was initially evaluated as a measure of metabolic fluxes through glycolysis (FIG. 4). The "G" valve had the largest impact on pyruvate production, with no detectable product measured in a control strain without SMVs. The improved production of pyruvate could be attributable either to a stoichiometric effect, wherein a portion of flux normally entering the TCA cycle is redistributed to the overflow metabolite, or alternatively to a more global increase in the sugar uptake rate enabling greater overflow metabolism and pyruvate synthesis. To evaluate these two alternatives we measured the impact of the "G" valve on glucose uptake rates. Results, shown in FIG. 4C, indicate that increases in pyruvate production are primarily attributed to increases in uptake rates rather than a repartitioning of basal fluxes.

Thus increased sugar uptake with the "G" valves was likely due to a direct regulatory effect of metabolites produced by the TCA cycle, namely α-ketoglutarate (αKG). αKG, a precursor to glutamic acid, has several key regulatory roles, including the regulation of sugar transport by direct inhibition of Enzyme I of the PTS dependent glucose transporter (FIG. 3). This feedback regulation is a way to coordinate sugar uptake with nitrogen assimilation (glutamate synthesis). We performed supplementation experiments, spiking 20 mM dimethyl-αKG (DM-αKG) into microfermentations at the onset of production. DM-αKG, rather than αKG was used as it has been shown to better cross the membrane, and after hydrolysis add to the intracellular αKG pool. As seen in FIG. 4, DM-αKG inhibited sugar uptake in control cells as well as in strains with valves reducing GltA levels. Together these results support dynamic reduction in GltA levels and the subsequent reduction in αKG pools as primarily responsible for improved sugar uptake rates and pyruvate biosynthesis. We next turned to assess pyruvate production in instrumented bioreactors. Minimal media fed batch fermentations were performed as previously reported by Menacho-Melgar et al. where phosphate concentration limited biomass levels and once consumed expression of the silencing gRNAs and the SspB chaperone are induced. Results comparing the control host strain with a strain having dynamic control over GltA levels are given in FIG. 4D. Minimal pyruvate transiently accumulated in the control strain whereas maximal titers of over 30 g/L were obtained using dynamic control.

To assess the impact of dynamic control over acetyl-CoA fluxes we leveraged citramalate synthase which produces one mole of citramalate from one mole of pyruvate and one mole of acetyl-CoA. Citramalate is a precursor to the industrial chemicals itaconic acid and methyl methacrylate, as well as an intermediate in branched chain amino acid biosynthesis. To produce citramalate, we used a low phosphate inducible plasmid expressing a previously reported feedback resistant mutant citramalate synthase (cimA3.7). This plasmid was introduced into the set of "G" and "Z" valve strains which were then assessed for citramalate production in two stage micro-fermentations (FIG. 5). The best producing strain had both "G" and "Z" valves.

Figure 4B:
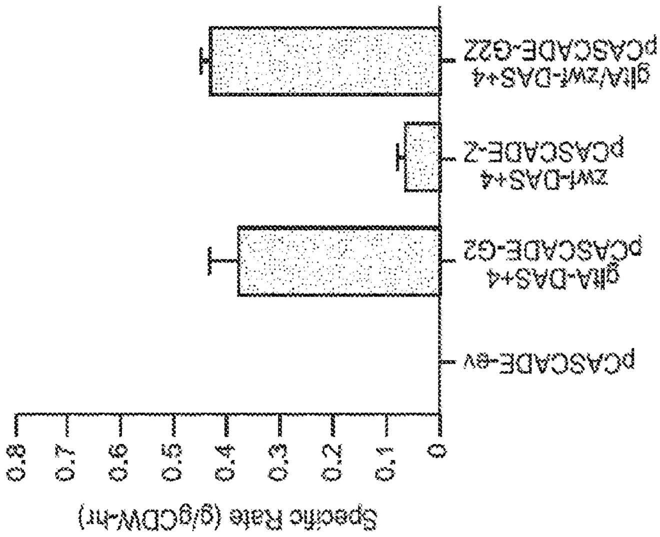
FIG. 4A-D: a) Dynamic reduction in GltA reduces αKG pools and alleviates αKG mediated inhibition of PTS-dependent glucose uptake (specifically, PtsI), improving glucose uptake rates, glycolytic fluxes and pyruvate production. b) The impact of dynamic control over GltA and Zwf levels on pyruvate production in minimal media microfermentations. c) The impact of dynamic control over GltA and Zwf levels and dimethyl-αKG supplementation on glucose uptake rates in microfermentations. (d) Pyruvate and biomass production were measured for the control strain and the "G" valve strain. The control strain's biomass (gray) and pyruvate production (blue), as well as the "G" valve strain's biomass (black) and pyruvate production (green) are plotted as a function of time. Dashed line represents extrapolated growth due to missed samples
Figure 4A:
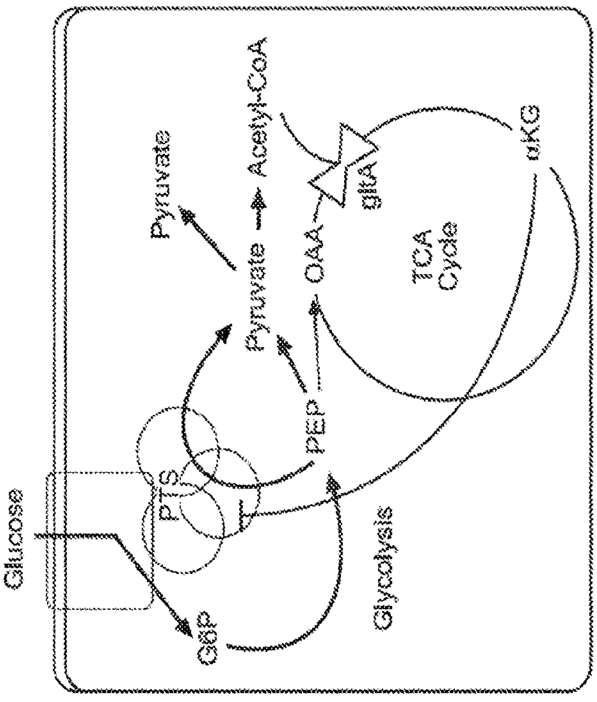
Figure 4D:
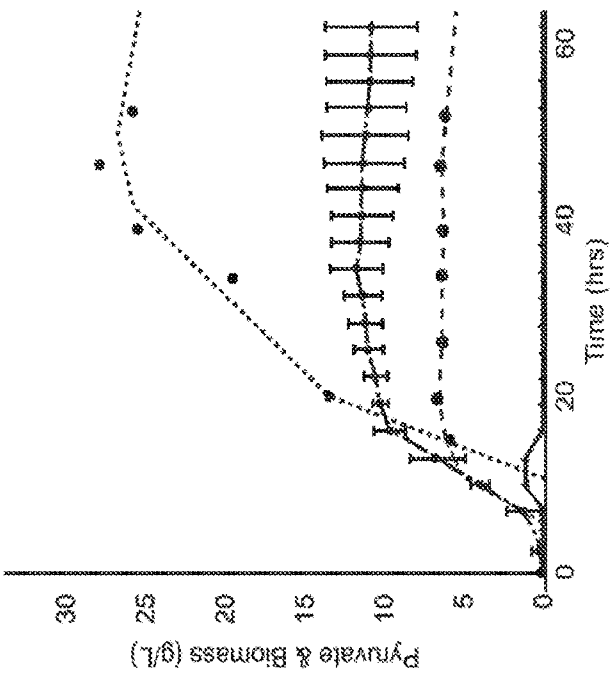
Figure 4C:
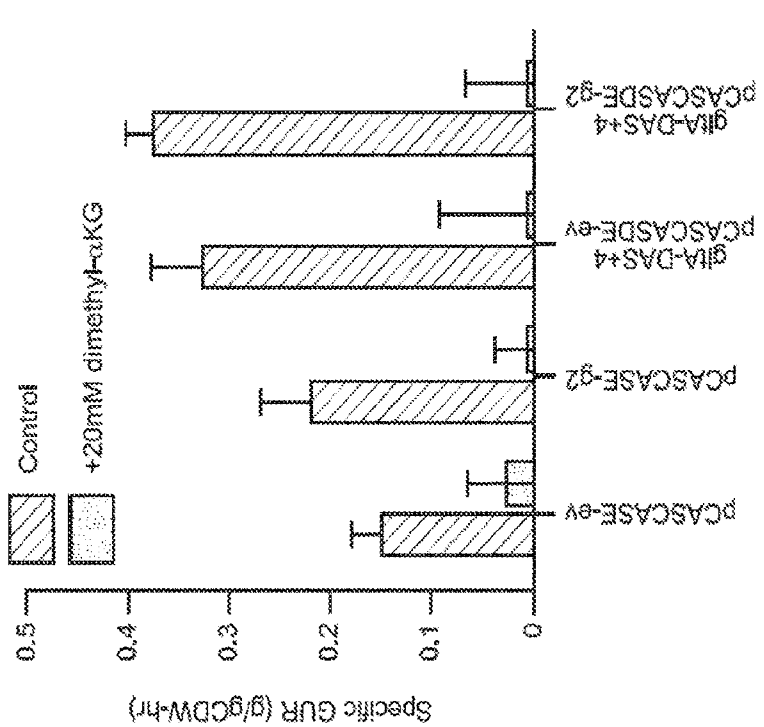

In the case of pyruvate, the "Z" valve had no significant impact on production (FIG. 4B). Citramalate and pyruvate are similar products in that they are both oxidized and require no redox cofactor (such as NADPH) for biosynthesis. A key difference in the two products is that citramalate requires an additional precursor, namely acetyl-CoA. The "Z-valve" dependent improvement in citramalate production may be dependent on improved acetyl-CoA production in strains with reduced Zwf activity. This would suggest that either Zwf levels or the levels of downstream metabolites have a negative regulatory impact on stationary phase acetyl-CoA synthesis. It is important to note that the strains used for pyruvate and citramalate production have deletions in poxB and pflB (which can lead to acetyl-CoA synthesis) and it was initially assumed all acetyl-CoA flux was through the well characterized pyruvate dehydrogenase (PDH) multienzyme complex. Unexpectedly, proteolytic degradation of Lpd (a subunit of PDH) had no impact on citramalate production. Based on this we considered the potential of an alternative primary route for acetyl-CoA production in stationary phase cultures, namely pyruvate-flavodoxin/ferredoxin oxidoreductase (Pfo), encoded by the ydbK gene.

Figure 5B:
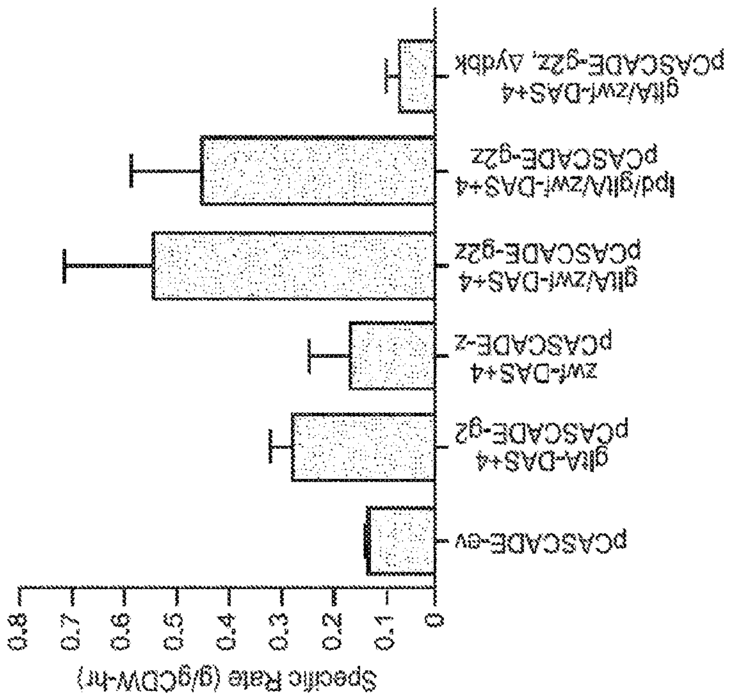
FIG. 5A-D: a) Dynamic reduction in Zwf levels activates the SoxRS regulon and increases activity of the pyruvate-ferredoxin oxidoreductase (Pfo, ydbK) improving acetyl-CoA fluxes and citramalate production. b) The impact of dynamic control over GltA and Zwf levels on citramalate production in minimal media microfermentations. Additionally, the proteolytic degradation of Lpd (lpd-DAS+4, a subunit of the pyruvate dehydrogenase multienzyme complex) and a deletion in ydbK were assessed in the "GZ" valve background. (c & d) Citramalate and biomass production were measured for the control strain (c) and the "GZ" valve strain (d). (c) Duplicate runs, biomass levels in gray and black, citramalate titers in green and blue. (d) The average of triplicate runs, biomass black and citramalate green. Dashed line represents extrapolated growth due to missed samples
Figure 5A:
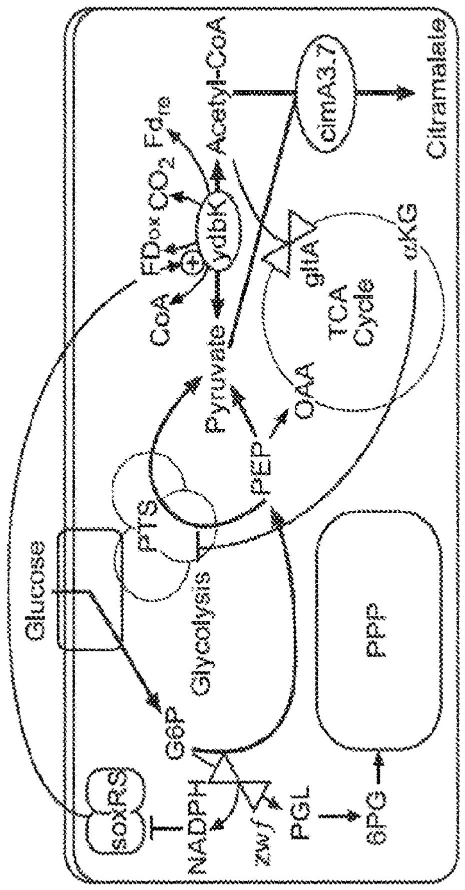
Figure 5D:
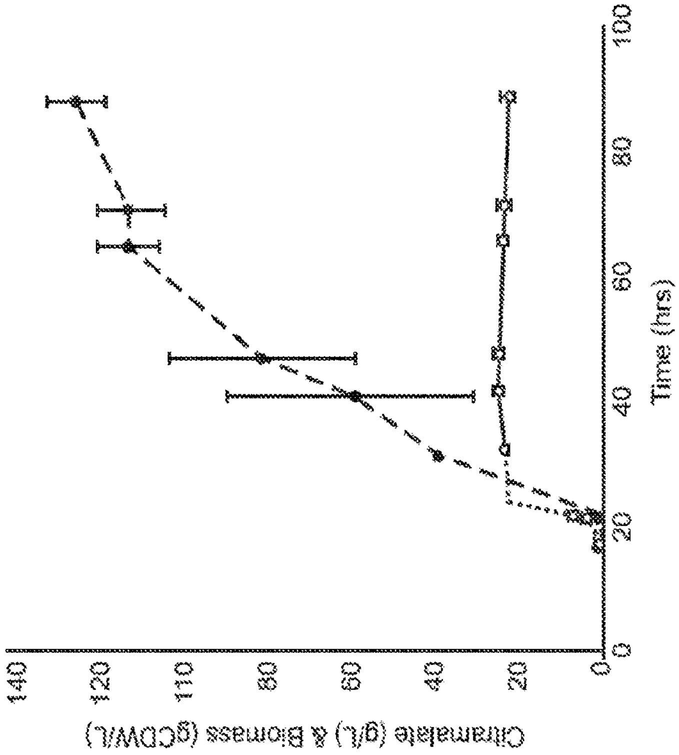

As illustrated in FIG. 3, that Pfo (ydbK) may be in part responsible for acetyl-CoA synthesis in stationary phase and that due to its role in the oxidative stress response this activity was regulated by intermediates in the PPP, also known to be involved in the response to oxidative stress. To test this hypothesis we constructed a ydbK deletion in the citramalate strain containing both "G" and "Z" valves and measured citramalate production. As seen in FIG. 5B, the deletion of ydbK significantly reduced citramalate synthesis confirming the role of Pfo in acetyl-CoA flux. As Pfo has been shown to be induced upon oxidative stress, via the SoxRS regulon (which is also regulated by NADPH pools), it may be that expression is due to alterations in NADPH levels caused by reductions in Zwf activity.

Figure 5C:
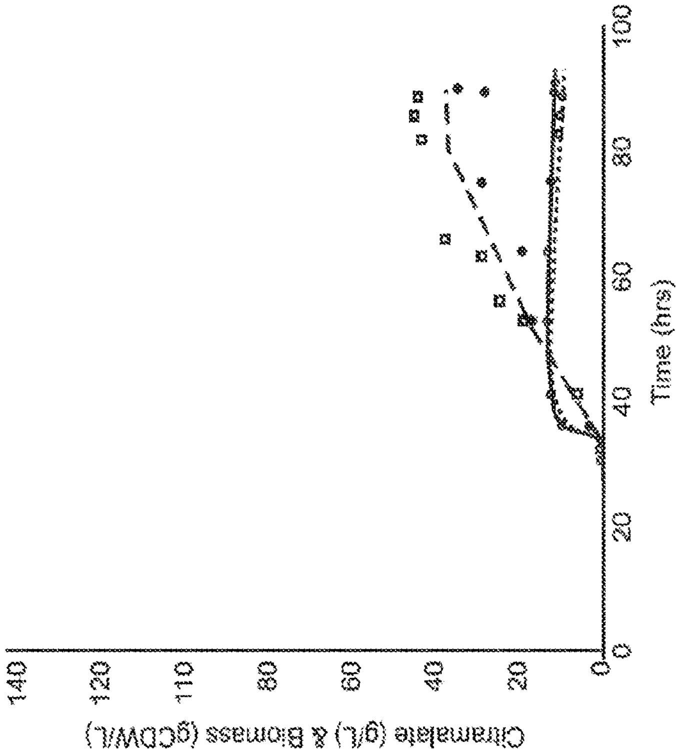
Figure 6A:
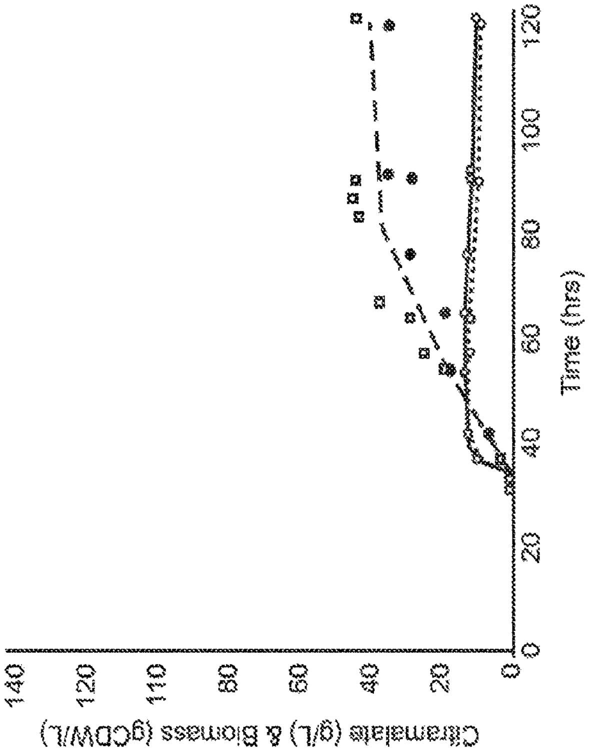
FIG. 6A-D: Citramalate and biomass production were measured for the control strain (a) and the "G" valve strain (b) and the "GZ" valve strain (c) in fermentations targeting biomass levels of 10 gCDW/L. Duplicate runs, biomass levels in gray and black, citramalate titers in green and blue. (d) Citramalate production and biomass levels in fermentations targeting biomass levels of 25 gCDW. The average of triplicate runs, biomass black and citramalate green. Dashed line represents extrapolated growth due to missed samples.
Figure 6B:
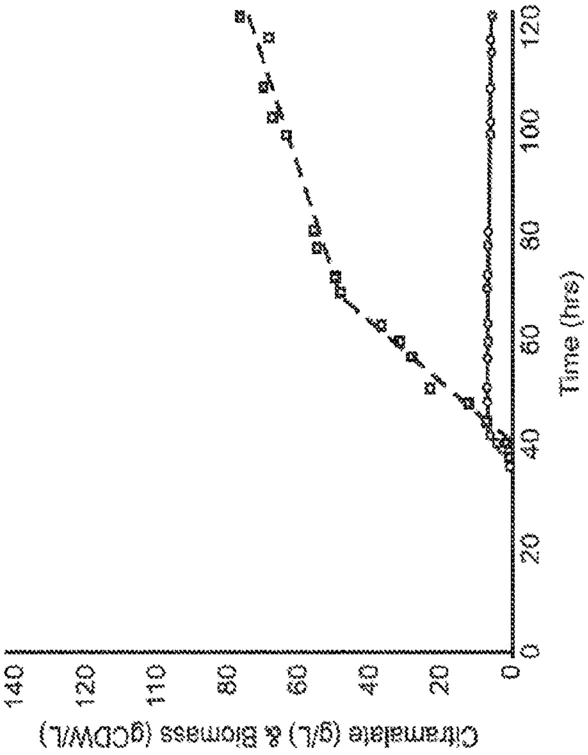
Figure 6C:
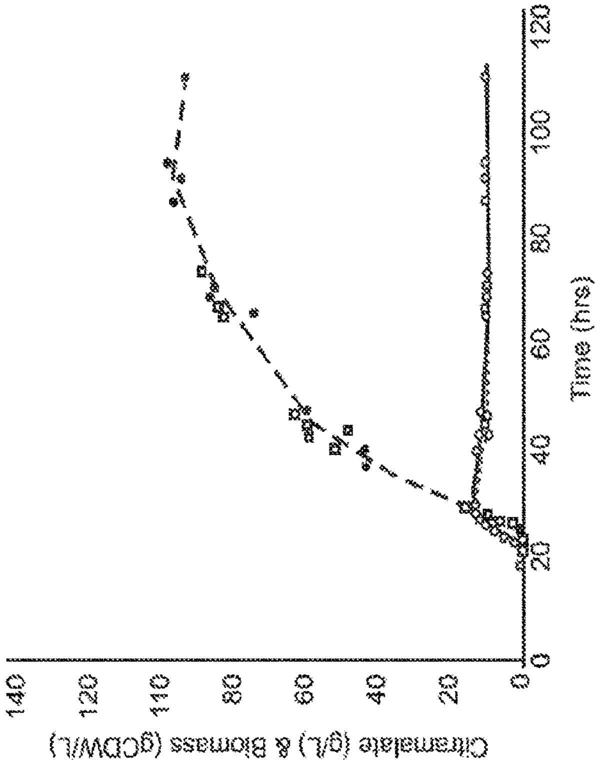
Figure 6D:
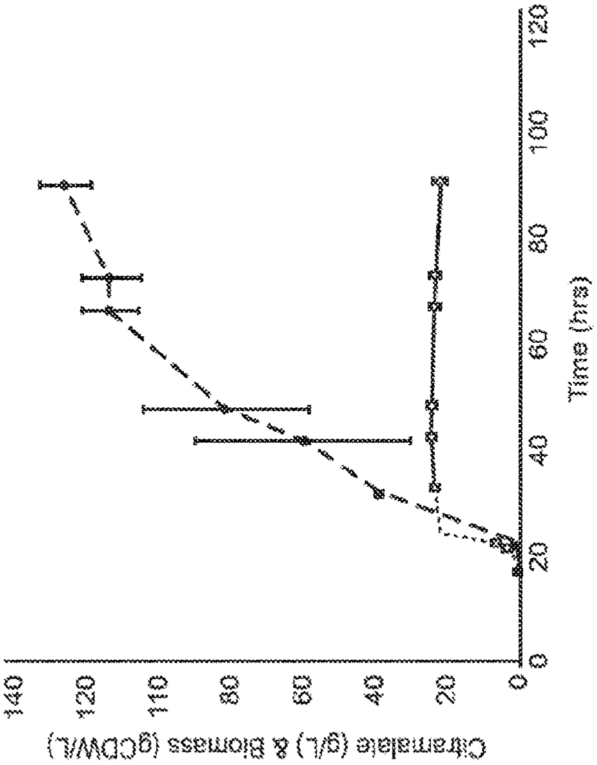
Figure 7A:
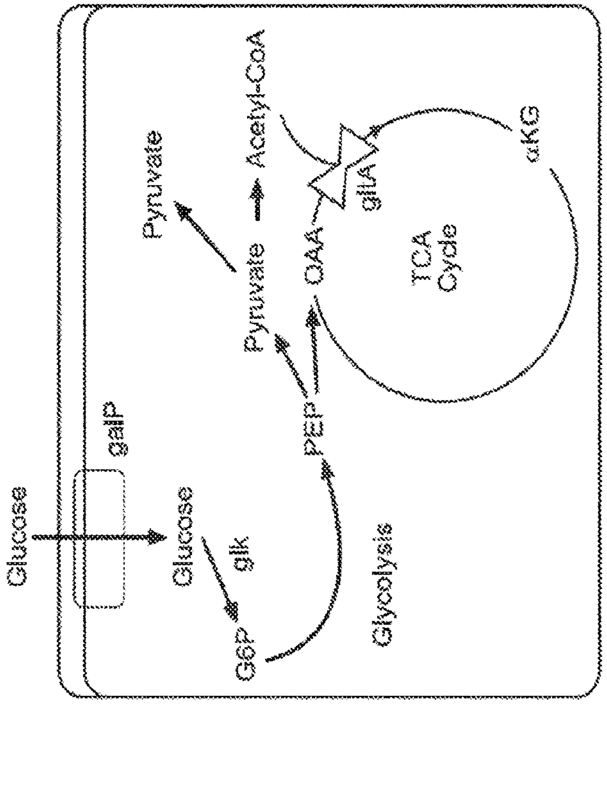
FIG. 7A-D: 7A) an overview of sugar uptake in a PTS minus strain of *E. coli*. 7B) Pyruvate production in 2-stage micro-fermentations in strain DLF_00286 and strain DLF_00286 with dynamic control of citrate synthase (GltA levels). 7C) Glucose uptake is insensitive to dimethyl-αKG supplementation in PTS(−) strains. 7D) Pyruvate and biomass production were measured for strain DLF 00286 and its "G" valve derivative.
Figure 7B:
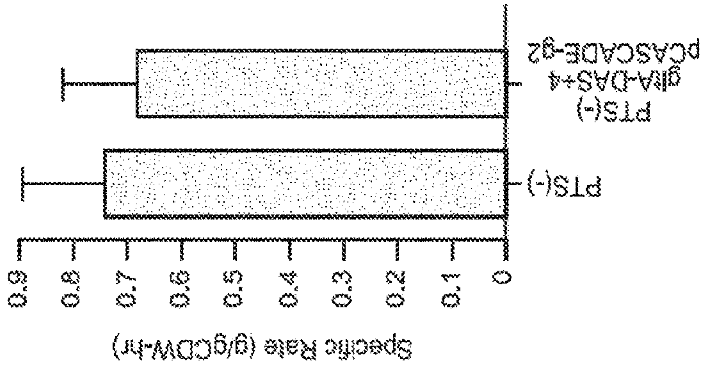
Figure 7D:
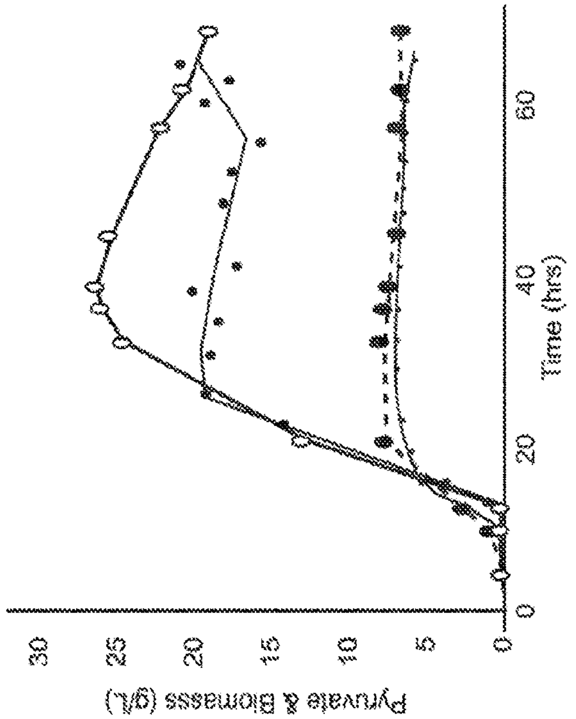
Figure 7C:
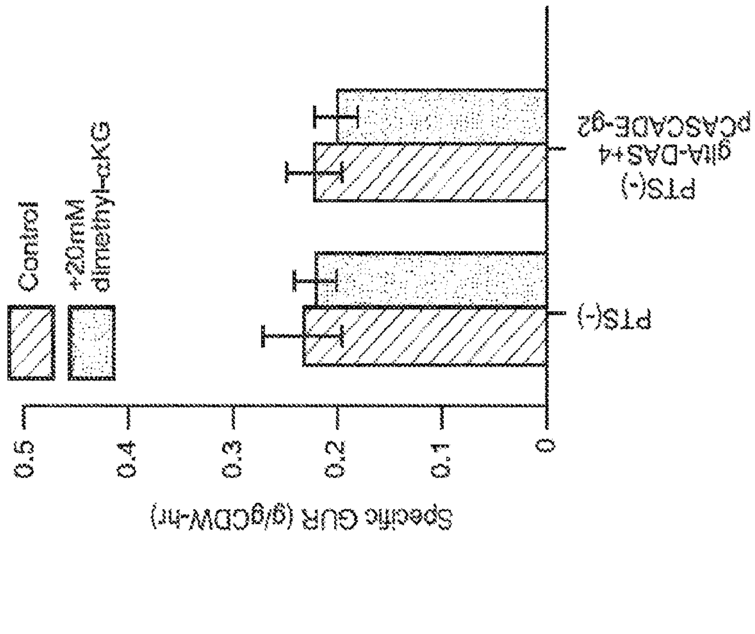

Lastly, we evaluated citramalate production strains in instrumented bioreactors. The control strain made reasonable citramalate titers (~40 g/L), whereas the introduction of SMVs improved production. The combined "GZ" valve strain had the highest citramalate production, reaching titers of ~100 g/L. This process was then intensified, by increasing biomass levels from ~10 gCDW/L to ~25 gCDW/L, leading to titers of 126+/−7 g/L. This process is illustrated in FIG. 5C. The overall process yields were 0.74-0.77 g citramalate/g glucose and during the production phase yields approached achieving 0.80-0.82 g citramalate/g glucose. The theoretical yield for citramalate from glucose is 1 mole/mole or 0.817 g/g.

Previous studies utilizing dynamic control have primarily been informed by a stoichiometric framework, wherein pathways are switched "ON" and "OFF" to reduce fluxes that stoichiometrically compete for a desired product, or in other words pathway redirection. For example Venayak and colleagues have highlighted the importance of GltA/CS as a central valve candidate for dynamic metabolic control, based in part on stoichiometric modelling. However these studies and models have missed the importance of the regulatory role of downstream metabolites, such as αKG. This work demonstrates that increasing flux by dysregulation of feedback control can have a large impact on production, independent of stoichiometry or the minimization of competing pathways. In particular, it was unexpected that reducing Zwf activity increases acetyl-CoA fluxes.

This is the first report of the interaction between minimal Zwf levels, SoxRS activation and Pfo activity in stationary phase. Additionally, the magnitude of the metabolic flux through Pfo is unexpected. Although Pfo, an iron sulfur cluster containing enzyme, has been successfully expressed in both aerobic and anaerobic conditions, it is quickly inactivated by molecular oxygen in vitro, and as a result, conventional wisdom would suggest it is unlikely to support these types of fluxes. These data suggest that the Pfo pathway can operate as a central metabolic pathway under certain conditions, and that high levels of activity can be maintained even aerobically in vivo. Improved understanding may lead to alternative strategies (independent of decreasing Zwf levels) for optimizing flux through this pathway, such as pathway overexpression and/or enzyme engineering.

Example 4: Stationary Phase Sugar Uptake and Pyruvate Synthesis is Insensitive to Alpha-Ketoglutarate Levels in a PTS-Minus Strain of *E. coli*

Referring now to FIG. 7, 0.7A) an overview of sugar uptake in a PTS minus strain of *E. coli*. Strain DLF_00286 (genotype F-, λ-, Δ(araD-araB)567, lacZ4787(del)(::rrnB-3), rph-1, Δ(rhaD-rhaB)568, hsdR514, ΔackA-pta, ΔpoxB, ΔpflB, ΔldhA, ΔadhE, ΔiclR, ΔarcA, ΔsspB, Δcas3::tm-ugpb-sspB-pro-casA, ΔptsG:glk, proDp-galP) has a mutation in the ptsG gene eliminating PTS-dependent glucose uptake. Glucose uptake is restored by overexpression of the galP galactose permease (which also can transport glucose) as well as glucokinase (glk) which activates glucose. FIG. 7B) Pyruvate production in 2-stage micro-fermentations in strain DLF_00286 and strain DLF_00286 with dynamic control of citrate synthase (GltA levels). Stationary phase pyruvate synthesis is improved in strain LF_00286 compared to the PTS(+) control (DLF_0025). Dynamic control of citrate synthase (gltA levels) does not improve pyruvate synthesis in the DLF_00286 host background. FIG. 7C) Glucose uptake is insensitive to dimethyl-αKG supplementation in PTS(−) strains. Stationary phase pyruvate synthesis is improved in strain LF_00286 compared to the PTS(+) control (DLF_0025). Dynamic control of citrate synthase (gltA levels) does not improve pyruvate synthesis in the DLF_00286 host background. FIG. 7D) Pyruvate and biomass production were measured for strain DLF_00286 and its "G" valve derivative. The control strain's biomass (gray) and pyruvate production (blue), as well as the "G" valve strain's biomass (black) and pyruvate production (green) are plotted as a function of time.

Example 5: Acetyl-CoA Flux is Dependent on Pfo (YdbK) Activity

Figure 8C:
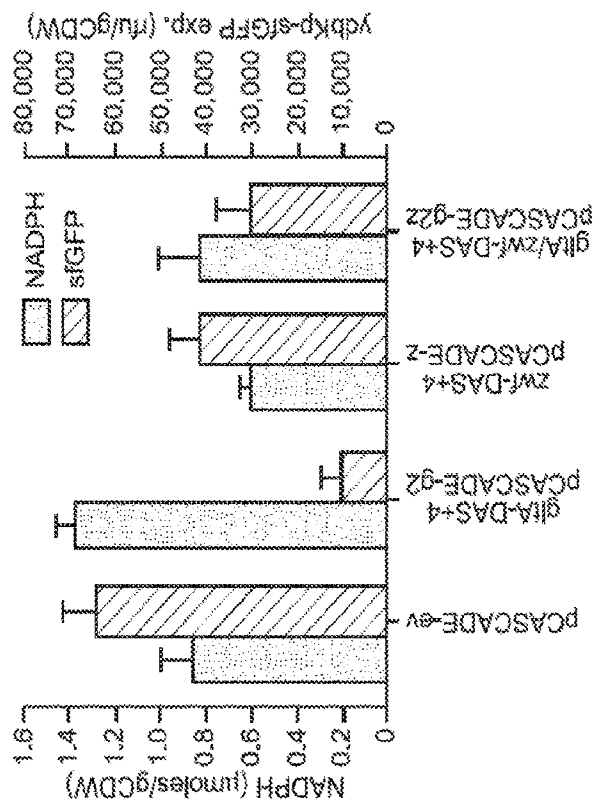
FIG. 8A-C: 8A) acetyl-CoA flux is dependent on Pfo (YdbK) activity 8B) relative stationary phase ydbK enzyme activity as a function of "G" and "Z" valves. 8C) NADPH pools (gray bars) and ydbK expression levels (green bars) in engineered strains.
Figure 8B:
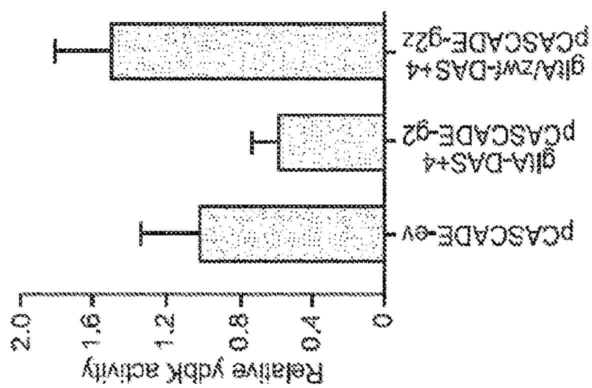
Figure 8A:
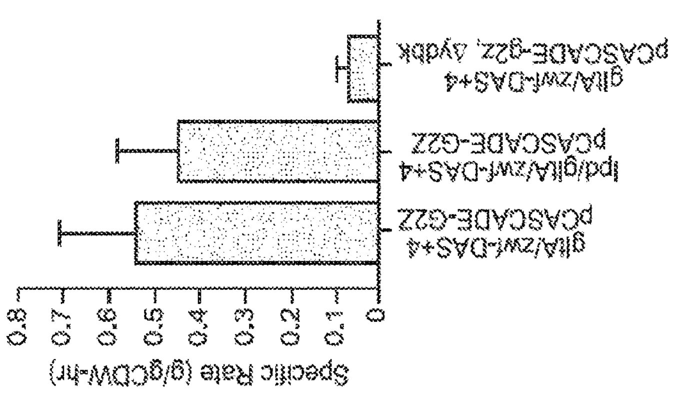

Referring now to FIG. 8A, the proteolytic degradation of Lpd (lpd-DAS+4, a subunit of the pyruvate dehydrogenase multienzyme complex and a deletion in ydbK were assessed in the "GZ" valve background. FIG. 8B demonstrates the relative stationary phase ydbK enzyme activity as a function of "G" and "Z" valves. ydbK activity was measured in crude lysates using pyruvate and CoA as substrates and methyl-viologen as an electron acceptor. In FIG. 8C) NADPH pools (gray bars) and ydbK expression levels (green bars) in engineered strains. Expression of a superfolder GFP (sfGFP) reporter is driven by the ydbK promoter.

Figure 9A:
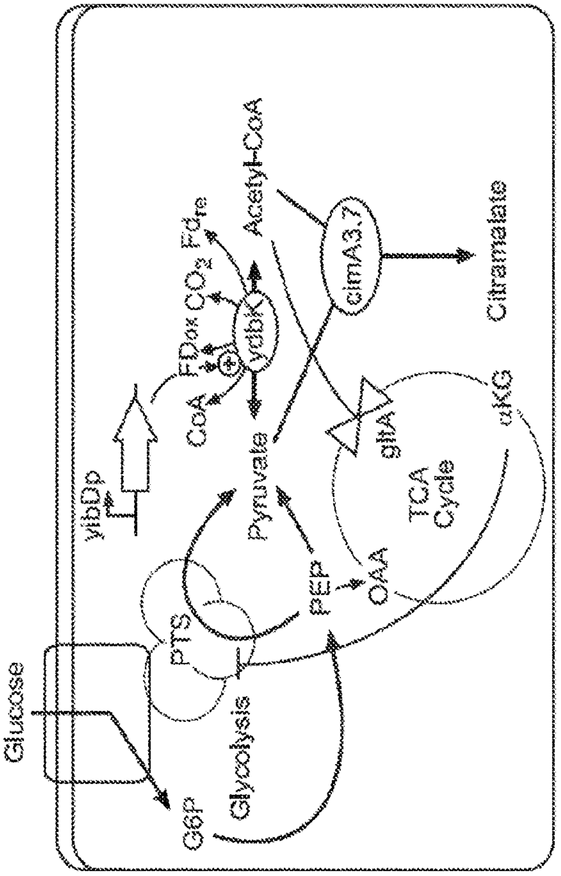
FIG. 9A-B Acetyl-CoA flux is dependent on soxS activation and can be improved independently of the "Z" valves. 9A) Strains were engineered for the low phosphate induction of SoxS (independent of NADPH pools and SoxR activation). 9B) Citramalate production in micro-fermentations in PTS(+) strains engineered with combinations of the "G" valve and low phosphate inducible soxS.
Figure 9B:
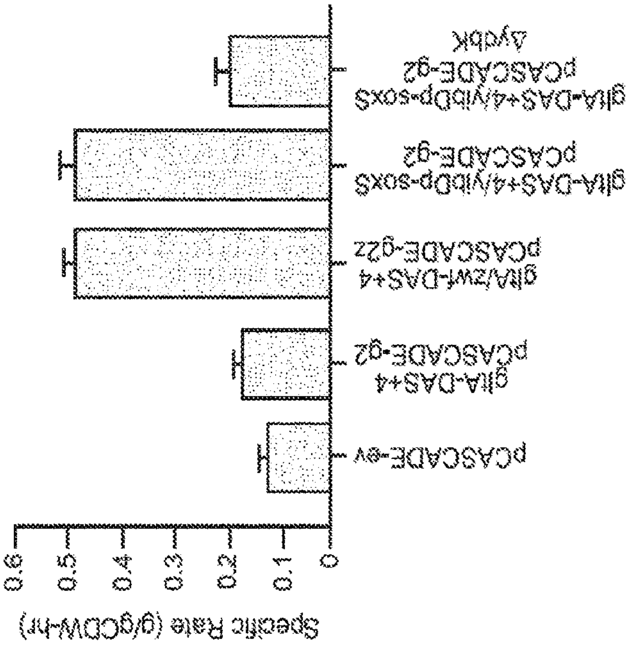

Example 6: Acetyl-CoA Flux is Dependent on soxS Activation and can be Improved Independently of the "Z" Valves Referring now to FIG. 9A, strains were engineered for the low phosphate induction of SoxS (independent of NADPH pools and SoxR activation). This was accomplished by engineering an extra copy of SoxS on the chromosome, induced by the low phosphate inducible yibD gene promoter. In FIG. 9B) Citramalate production in micro-fermentations in PTS(+) strains engineered with combinations of the "G" valve and low phosphate inducible soxS. Importantly, deletion of ydbK in a strain with soxS induction still reduces citramalate flux.

More generally, this invention highlights the potential of manipulating known and unknown feedback regulatory mechanisms to improve in vivo enzyme activities and metabolic fluxes. This approach can open numerous novel engineering strategies, and leads to significant improvements in production rates, titers and yields. Furthermore these results confirm the metabolic potential of stationary phase cultures. Dynamic metabolic control in two-stage cultures is uniquely suited to implement these strategies. Simply overexpressing key enzymes does not bypass native regulation and the complete removal of central metabolic enzymes and/or metabolites will often lead to growth defects and strains which need to evolve compensatory metabolic changes to meet the demands of growth. In contrast changes to levels of central regulatory metabolites in stationary phase enable rewiring of the regulatory network and metabolic fluxes without this constraint.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept

The invention claimed is:

1. A genetically modified *E. coli* microorganism comprising:

a production pathway comprising citramalate synthase for the production of citramalate, a conditional induction of SoxS by depletion of a limiting nutrient from a growth medium in which the genetically modified microorganism is growing; and a conditionally triggered synthetic metabolic valve that silences gene expression of the glucose-6-phosphate-dehydrogenase (zwf) gene; or a conditionally triggered synthetic metabolic valve that enables selective proteolysis of the glucose-6-phosphate-dehydrogenase (zwf) enzyme;

wherein the synthetic metabolic valve(s) and induction of SoxS in the microorganism are conditionally triggered during a stationary phase or non-dividing cellular state;

wherein, under conditions of depleting of a limiting nutrient from a growth medium in which the genetically modified microorganism is growing, a stationary phase or non-dividing cellular state is induced;

wherein pyruvate-flavodoxin/ferredoxin oxidoreductase enzyme activity is overexpressed upon depletion of a limiting nutrient from a growth medium in which the genetically modified microorganism is growing during the stationary phase or non-dividing cellular state to produce an acetyl CoA pool; and wherein PTS-dependent glucose uptake is enhanced within the genetically modified microorganism, when compared to a non-genetically modified microorganism.

2. The genetically modified microorganism of claim 1, wherein the genetically modified microorganism comprises deletion of endogenous pyruvate oxidase (poxB) and pyruvate-formate lyase (pflB) genes.

3. The genetically modified microorganism of claim 1, wherein the pyruvate-flavodoxin/ferredoxin oxidoreductase enzyme is encoded by the ydbK gene.

4. The genetically modified microorganism of claim 1, wherein the increased pyruvate ferredoxin oxidoreductase enzyme activity is due to induction of the oxidative soxRS regulon during the stationary phase or non-dividing cellular state.

5. The genetically modified microorganism of claim 1, wherein the increased pyruvate ferredoxin oxidoreductase enzyme activity is increased as the result of reduced NADPH levels within the genetically modified microorganism during the stationary phase or non-dividing cellular state.

6. The genetically modified microorganism of claim 1, wherein the PTS-dependent glucose uptake activity increases during a stationary phase or non-dividing cellular state.

7. The genetically modified microorganism of claim 6, wherein the PTS-dependent glucose uptake is encoded by a pts gene.

8. The genetically modified *E. coli* microorganism of claim 1, wherein the synthetic metabolic valves effect gene silencing by CRISPR interference, synthetic metabolic valves further comprising a CASCADE guide array, the array comprising two or more genes encoding small guide RNAs each specific for targeting a different gene for simultaneous silencing of multiple genes, the guide array comprising more than one promotor for each gene.

9. A bioprocess for production of a chemical product from the genetically modified microorganism of claim 1, the bioprocess comprising:

in a first stage, growing the genetically modified microorganism in a medium and in a second stage, upon depletion of a limiting nutrient from a growth medium, inducing a stationary phase or non-dividing cellular state, wherein the genetically modified microorganism in the stationary phase or non-dividing cellular state produces product at a rate of 30 g/L or greater per 24 hours.

10. The bioprocess of claim 9, wherein the increased activity of a pyruvate-flavodoxin/ferredoxin oxidoreductase enzyme is caused by overexpression of a gene encoding an active pyruvate ferredoxin oxidoreductase, induction of the oxidative soxRS regulon, reducing NADPH levels, reducing glucose-6-phosphate dehydrogenase levels with a synthetic metabolic valve directed to gene silencing of the zwf gene or selective proteolysis of the glucose-6-phosphate dehydrogenase enzyme, the valve activated in the stationary phase or non-dividing cellular state, or a combination thereof.

11. The bioprocess of claim 9, where the citramalate synthase enzyme is encoded by the cimA3.7 gene.

12. The bioprocess of claim 9, wherein the genetically modified microorganism comprises a plasmid comprising a citramalate synthase gene is operably linked to a low phosphate inducible promotor.

13. A genetically modified *E. coli* microorganism comprising:

a production pathway comprising at least one enzyme for producing a product from an acetyl CoA precursor, and a conditional induction of SoxS depletion of a limiting nutrient from a growth medium in which the genetically modified microorganism is growing;

a conditionally triggered synthetic metabolic valve that silences gene expression of the glucose-6-phosphate-dehydrogenase (zwf) gene; or a conditionally triggered synthetic metabolic valve that enables selective proteolysis of the glucose-6-phosphate-dehydrogenase (zwf) enzyme;

deletion of endogenous pyruvate oxidase (poxB) and pyruvate-formate lyase (pflB) genes genes;

wherein the synthetic metabolic valve(s) and induction of SoxS in the microorganism are conditionally triggered during a stationary phase or non-dividing cellular state;

wherein, under conditions of depleting of a limiting nutrient from a growth medium in which the genetically modified microorganism is growing, a stationary phase or non-dividing cellular state is induced;

wherein pyruvate-flavodoxin/ferredoxin oxidoreductase enzyme activity is overexpressed upon depletion of a limiting nutrient from a growth medium in which the genetically modified microorganism is growing during the stationary phase or non-dividing cellular state to produce an acetyl CoA pool; and wherein PTS-dependent glucose uptake is enhanced within the genetically modified microorganism, when compared to a non-genetically modified microorganism.

14. The genetically modified microorganism of claim 13, wherein the pyruvate-flavodoxin/ferredoxin oxidoreductase enzyme is encoded by the ydbK gene.

15. The genetically modified microorganism of claim 13, wherein the PTS-dependent glucose uptake is encoded by a pts gene.

16. The genetically modified microorganism of claim 13, wherein the product is pyruvate.

17. The bioprocess of claim 13, wherein the product is citramalate, an enzyme of the production pathway comprises citramalate synthase, and the bioprocess produces citramalate at or greater than 100 g/L per 24 hours.

* * * * *

SEQUENCE LISTING

```
<160> NUMBER OF SEQ ID NOS: 40

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1

ctggtacacg ctgatgaaca cc                                              22


<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2

ctggtcattg ccatttgtgc c                                               21
```

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
gaatcagagc gttccgaccc 20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gtacgcagtt tgccaacgtg 20

<210> SEQ ID NO 5
<211> LENGTH: 74
<212> TYPE: DNA
<213> ORGANISM: Artificial Sequence
<220> FEATURE:
<223> OTHER INFORMATION: Synthetic

<400> SEQUENCE: 5
aatagcccgc tgatatcatc gataatacta aaaaaacagg gaggctatta tcctaatttt 60
tgttgacact ctat 74

<210> SEQ ID NO 6
<211> LENGTH: 27
<212> TYPE: DNA
<213> ORGANISM: Artificial Sequence
<220> FEATURE:
<223> OTHER INFORMATION: Synthetic

<400> SEQUENCE: 6
caagacatgt gtatatcact gtaattc 27

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
gcgattgcag atttatgatt tgg 23

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tatcatcctg aaagcgatgg 20

<210> SEQ ID NO 9
<211> LENGTH: 17
<212> TYPE: DNA
<213> ORGANISM: Artificial Sequence
<220> FEATURE:

<223> OTHER INFORMATION: Synthetic

<400> SEQUENCE: 9
ctgctggaaa ccatgcg 17

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
gagcatggtg atcttctcag t 21

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
actgaagccc agacgatc 18

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
atctcaccgt gtgatcgg 18

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
gcgatgaatg tcttactacg ga 22

<210> SEQ ID NO 14
<211> LENGTH: 3527
<212> TYPE: DNA
<213> ORGANISM: Artificial Sequence
<220> FEATURE:
<223> OTHER INFORMATION: Synthetic

<400> SEQUENCE: 14
tcctaatttt tgttgacact ctatcattga tagagttatt ttaccactcc ctatcagtga 60
tagagaaaag tgaaatgaat agttcgacaa agatcgcatt ggtaattacg ttactcgatg 120
ccatggggat tggccttatc atgccagtct tgccaacgtt attacgtgaa tttattgctt 180
cggaagatat cgctaaccac tttggcgtat tgcttgcact ttatgcgtta atgcaggtta 240
tctttgctcc ttggcttgga aaaatgtctg accgatttgg tcggcgccca gtgctgttgt 300
tgtcattaat aggcgcatcg ctggattact tattgctggc tttttcaagt gcgctttgga 360
tgctgtattt aggccgtttg ctttcaggga tcacaggagc tactggggct gtcgcggcat 420
cggtcattgc cgataccacc tcagcttctc aacgcgtgaa gtggttcggt tggttagggg 480

```
caagttttgg gcttggttta atagcggggc ctattattgg tggttttgca ggagagattt    540
caccgcatag tccctttttt atcgctgcgt tgctaaatat tgtcactttc cttgtggtta    600
tgttttggtt ccgtgaaacc aaaaatacac gtgataatac agataccgaa gtaggggttg    660
agacgcaatc gaattcggta tacatcactt tatttaaaac gatgcccatt ttgttgatta    720
tttatttttc agcgcaattg ataggccaaa ttcccgcaac ggtgtgggtg ctatttaccg    780
aaaatcgttt tggatggaat agcatgatgg ttggcttttc attagcgggt cttggtcttt    840
tacactcagt attccaagcc tttgtggcag gaagaatagc cactaaatgg ggcgaaaaaa    900
cggcagtact gctcggattt attgcagata gtagtgcatt tgcctttta gcgtttatat    960
ctgaaggttg gttagtttc cctgttttaa ttttattggc tggtggtggg atcgctttac   1020
ctgcattaca gggagtgatg tctatccaaa caaagagtca tcagcaaggt gctttacagg   1080
gattattggt gagccttacc aatgcaaccg gtgttattgg cccattactg tttgctgtta   1140
tttataatca ttcactacca atttgggatg gctggatttg gattattggt ttagcgtttt   1200
actgtattat tatcctgcta tcgatgacct tcatgttaac ccctcaagct caggggagta   1260
aacaggagac aagtgcttag ttatttcgtc accaaatgat gttattccgc gaaatataat   1320
gaccctcttg ataacccaag agcatcacat atacctgccg ttcactatta tttagtgaaa   1380
tgagatatta tgatattttc tgaattgtga ttaaaaaggc aactttatgc ccatgcaaca   1440
gaaactataa aaaatacaga gaatgaaaag aaacagatag attttttagt tctttaggcc   1500
cgtagtctgc aaatcctttt atgattttct atcaaacaaa agaggaaaat agaccagttg   1560
caatccaaac gagagtctaa tagaatgagg tcgaaaagta aatcgcgcgg gtttgttact   1620
gataaagcag gcaagaccta aaatgtgtaa agggcaaagt gtatactttg gcgtcacccc   1680
ttacatattt taggtctttt tttattgtgc gtaactaact tgccatcttc aaacaggagg   1740
gctggaagaa gcagaccgct aacacagtac ataaaaaagg agacatgaac gatgaacatc   1800
aaaaagtttg caaaacaagc aacagtatta acctttacta ccgcactgct ggcaggaggc   1860
gcaactcaag cgtttgcgaa agaaacgaac caaaagccat ataaggaaac atacggcatt   1920
tcccatatta cacgccatga tatgctgcaa atccctgaac agcaaaaaaa tgaaaaatat   1980
caagttcctg agttcgattc gtccacaatt aaaaatatct cttctgcaaa aggcctggac   2040
gtttgggaca gctggccatt acaaaacgct gacggcactg tcgcaaacta tcacggctac   2100
cacatcgtct ttgcattagc cggagatcct aaaaatgcgg atgacacatc gatttacatg   2160
ttctatcaaa aagtcggcga aacttctatt gacagctgga aaaacgctgg ccgcgtcttt   2220
aaagacagcg acaaattcga tgcaaatgat tctatcctaa aagaccaaac acaagaatgg   2280
tcaggttcag ccacatttac atctgacgga aaaatccgtt tattctacac tgatttctcc   2340
ggtaaacatt acggcaaaca aacactgaca actgcacaag ttaacgtatc agcatcagac   2400
agctctttga acatcaacgg tgtagaggat tataaatcaa tctttgacgg tgacggaaaa   2460
acgtatcaaa atgtacagca gttcatcgat gaaggcaact acagctcagg cgacaaccat   2520
acgctgagag atcctcacta cgtagaagat aaaggccaca aatacttagt atttgaagca   2580
aacactggaa ctgaagatgg ctaccaaggc gaagaatctt tatttaacaa agcatactat   2640
ggcaaaagca catcattctt ccgtcaagaa agtcaaaaac ttctgcaaag cgataaaaaa   2700
cgcacggctg agttagcaaa cggcgctctc ggtatgattg agctaaacga tgattacaca   2760
ctgaaaaaag tgatgaaacc gctgattgca tctaacacag taacagatga aattgaacgc   2820
```

gcgaacgtct ttaaaatgaa cggcaaatgg tacctgttca ctgactcccg cggatcaaaa 2880
atgacgattg acggcattac gtctaacgat atttacatgc ttggttatgt ttctaattct 2940
ttaactggcc catacaagcc gctgaacaaa actggccttg tgttaaaaat ggatcttgat 3000
cctaacgatg taacctttac ttactcacac ttcgctgtac ctcaagcgaa aggaaacaat 3060
gtcgtgatta caagctatat gacaaacaga ggattctacg cagacaaaca atcaacgttt 3120
gcgccaagct tcctgctgaa catcaaaggc aagaaaacat ctgttgtcaa agacagcatc 3180
cttgaacaag gacaattaac agttaacaaa taaaaacgca aaagaaaatg ccgatattga 3240
ctaccggaag cagtgtgacc gtgtgcttct caaatgcctg attcaggctg tctatgtgtg 3300
actgttgagc tgtaacaagt tgtctcaggt gttcaatttc atgttctagt tgctttgttt 3360
tactggtttc acctgttcta ttaggtgtta catgctgttc atctgttaca ttgtcgatct 3420
gttcatggtg aacagcttta aatgcaccaa aaactcgtaa aagctctgat gtatctatct 3480
tttttacacc gttttcatct gtgcatatgg acagttttcc ctttgat 3527

<210> SEQ ID NO 15
<211> LENGTH: 476
<212> TYPE: DNA
<213> ORGANISM: Artificial Sequence
<220> FEATURE:
<223> OTHER INFORMATION: Synthetic

<400> SEQUENCE: 15
caagacatgt gtatatcact gtaattcgat atttatgagc agcatcgaaa aatagcccgc 60
tgatatcatc gataatacta aaaaaacagg gaggctatta ccaggcatca aataaaacga 120
aaggctcagt cgaaagactg ggcctttcgt tttatctgtt gtttgtcggt gaacgctctc 180
tactagagtc acactggctc accttcgggt gggcctttct gcgtttatat ctttctgaca 240
ccttactatc ttacaaatgt aacaaaaaag ttatttttct gtaattcgag catgtcatgt 300
taccccgcga gcataaaacg cgtgtgtagg aggataatct ttgacggcta gctcagtcct 360
aggtacagtg ctagccatat gaaggagaac aaatgaattt gcttattgat aactggatcc 420
ctgtacgccc gcgaaacggg gggaaagtcc aaatcataaa tctgcaatcg ctatac 476

<210> SEQ ID NO 16
<211> LENGTH: 974
<212> TYPE: DNA
<213> ORGANISM: Artificial Sequence
<220> FEATURE:
<223> OTHER INFORMATION: Synthetic

<400> SEQUENCE: 16
caagacatgt gtatatcact gtaattcgat atttatgagc agcatcgaaa aatagcccgc 60
tgatatcatc gataatacta aaaaaacagg gaggctatta ccaggcatca aataaaacga 120
aaggctcagt cgaaagactg ggcctttcgt tttatctgtt gtttgtcggt gaacgctctc 180
tactagagtc acactggctc accttcgggt gggcctttct gcgtttatat ctttctgaca 240
ccttactatc ttacaaatgt aacaaaaaag ttatttttct gtaattcgag catgtcatgt 300
taccccgcga gcataaaacg cgtgtgtagg aggataatct atggatttgt cacagctaac 360
accacgtcgt ccctatctgc tgcgtgcatt ctatgagtgg ttgctggata accagctcac 420
gccgcacctg gtggtggatg tgacgctccc tggcgtgcag gttcctatgg aatatgcgcg 480
tgacgggcaa atcgtactca acattgcgcc gcgtgctgtc ggcaatctgg aactggcgaa 540
tgatgaggtg cgctttaacg cgcgctttgg tggcattccg cgtcaggttt ctgtgccgct 600
ggctgccgtg ctggctatct acgcccgtga aaatggcgca ggcacgatgt ttgagcctga 660
agctgcctac gatgaagata ccagcatcat gaatgatgaa gaggcatcgg cagacaacga 720
aaccgttatg tcggttattg atggcgacaa gccagatcac gatgatgaca ctcatcctga 780
cgatgaacct ccgcagccac cacgcggtgg tcgaccggca ttacgcgttg tgaagtaatt 840
gacggctagc tcagtcctag gtacagtgct agccatatga aggagaacaa atgaatttgc 900
ttattgataa ctggatccct gtacgcccgc gaaacggggg gaaagtccaa atcataaatc 960
tgcaatcgct atac 974

<210> SEQ ID NO 17
<211> LENGTH: 869
<212> TYPE: DNA
<213> ORGANISM: Artificial Sequence
<220> FEATURE:
<223> OTHER INFORMATION: Synthetic

<400> SEQUENCE: 17
gtattccgtc ttccatgttc accgtcattt tcgcaatggc acgtaccgtt ggctggatcg 60
cccactggag cgaaatgcac agtgacggta tgaagattgc ccgtccgcgt cagctgtata 120
caggatatga aaaacgcgac tttaaaagcg atatcaagcg tgcggccaac gatgaaaact 180
attctgaaaa ctatgcggat gcgtcttaat agttgacaat taatcatcgg catagtatat 240
cggcatagta taatacgact cactatagga gggccatcat ggccaagttg accagtgccg 300
ttccggtgct caccgcgcgc gacgtcgccg gagcggtcga gttctggacc gaccggctcg 360
ggttctcccg ggacttcgtg gaggacgact tcgccggtgt ggtccgggac gacgtgaccc 420
tgttcatcag cgcggtccag gaccaggtgg tgccggacaa caccctggcc tgggtgtggg 480
tgcgcggcct ggacgagctg tacgccgagt ggtcggaggt cgtgtccacg aacttccggg 540
acgcctccgg gccggccatg accgagatcg gcgagcagcc gtgggggcgg gagttcgccc 600
tgcgcgaccc ggccggcaac tgcgtgcact ttgtggcaga ggagcaggac tgaggataag 660
taatggttga ttgctaagtt gtaaatattt taacccgccg ttcatatggc gggttgattt 720
ttatatgcct aaacacaaaa aattgtaaaa ataaaatcca ttaacagacc tatatagata 780
tttaaaaaga atagaacagc tcaaattatc agcaacccaa tactttcaat taaaaacttc 840
atggtagtcg catttataac cctatgaaa 869

<210> SEQ ID NO 18
<211> LENGTH: 1702
<212> TYPE: DNA
<213> ORGANISM: Artificial Sequence
<220> FEATURE:
<223> OTHER INFORMATION: Synthetic

<400> SEQUENCE: 18
aacgtcgatt tctactctgg tatcatcctg aaagcgatgg gtattccgtc ttccatgttc 60
accgtcattt tcgcaatggc acgtaccgtt ggctggatcg cccactggag cgaaatgcac 120
agtgacggta tgaagattgc ccgtccgcgt cagctgtata caggatatga aaaacgcgac 180
tttaaaagcg atatcaagcg tgggggttca ggcgggtcgg gtggcgtgag caagggcgag 240
gagctgttca ccggggtggt gcccatcctg gtcgagctgg acggcgacgt aaacggccac 300
aagttcagcg tgcgcggcga gggcgagggc gatgccacca acggcaagct gaccctgaag 360
ttcatctgca ccaccggcaa gctgcccgtg ccctggccca ccctcgtgac caccctgacc 420

-continued tacggcgtgc agtgcttcag ccgctacccc gaccacatga agcgccacga cttcttcaag 480
tccgccatgc ccgaaggcta cgtccaggag cgcaccatca gcttcaagga cgacggcacc 540
tacaagaccc gcgccgaggt gaagttcgag ggcgacaccc tggtgaaccg catcgagctg 600
aagggcatcg acttcaagga ggacggcaac atcctggggc acaagctgga gtacaacttc 660
aacagccaca acgtctatat caccgccgac aagcagaaga acggcatcaa ggccaacttc 720
aagatccgcc acaacgtgga ggacggcagc gtgcagctcg ccgaccacta ccagcagaac 780
acccccatcg gcgacggccc cgtgctgctg cccgacaacc actacctgag cacccagtcc 840
gtgctgagca aagaccccaa cgagaagcgc gatcacatgg tcctgctgga gttcgtgacc 900
gccgccggga tcactcacgg catggacgag ctgtacaagt aatgatgatc ggcacgtaag 960
aggttccaac tttcaccata atgaaataag atcactaccg ggcgtatttt ttgagttatc 1020
gagattttca ggagctaagg aagctaaaat ggctaaactg acgtcggccg ttccagtgct 1080
tactgcgcgt gatgtagcgg gagccgtaga gttttggacg gatcgtcttg ggtttagtcg 1140
cgactttgtg gaagatgact tcgcagggt tgttcgtgat gacgtcacac tgttcatcag 1200
tgccgtacag gatcaggttg tacccgataa cactcttgcg tgggtatggg tgcgtggcct 1260
ggatgagtta tacgccgaat ggtccgaggt agtcagcaca aacttccgcg acgcatccgg 1320
gcccgctatg actgagatcg gggaacaacc gtggggacgt gagtttgcct tacgtgaccc 1380
ggcggggaac tgcgtccact ttgtggcgga ggagcaggac taaggataag tagtggttga 1440
ttgctaagtt gtaaatattt taacccgccg ttcatatggc gggttgattt ttatatgcct 1500
aaacacaaaa aattgtaaaa ataaaatcca ttaacagacc tatatagata tttaaaaaga 1560
atagaacagc tcaaattatc agcaacccaa tactttcaat taaaaacttc atggtagtcg 1620
catttataac cctatgaaaa tgacgtctat ctataccccc ctatatttta ttcatcatac 1680
aacaaattca tgataccaat aa 1702

<210> SEQ ID NO 19
<211> LENGTH: 1777
<212> TYPE: DNA
<213> ORGANISM: Artificial Sequence
<220> FEATURE:
<223> OTHER INFORMATION: Synthetic

<400> SEQUENCE: 19
aacgtcgatt tctactctgg tatcatcctg aaagcgatgg gtattccgtc ttccatgttc 60
accgtcattt tcgcaatggc acgtaccgtt ggctggatcg cccactggag cgaaatgcac 120
agtgacggta tgaagattgc ccgtccgcgt cagctgtata caggatatga aaaacgcgac 180
tttaaaagcg atatcaagcg tgggggttca ggcgggtcgg gtggcgtgag caagggcgag 240
gagctgttca ccggggtggt gcccatcctg gtcgagctgg acggcgacgt aaacggccac 300
aagttcagcg tgcgcggcga gggcgagggc gatgccacca acggcaagct gaccctgaag 360
ttcatctgca ccaccggcaa gctgcccgtg ccctggccca ccctcgtgac caccctgacc 420
tacggcgtgc agtgcttcag ccgctacccc gaccacatga agcgccacga cttcttcaag 480
tccgccatgc ccgaaggcta cgtccaggag cgcaccatca gcttcaagga cgacggcacc 540
tacaagaccc gcgccgaggt gaagttcgag ggcgacaccc tggtgaaccg catcgagctg 600
aagggcatcg acttcaagga ggacggcaac atcctggggc acaagctgga gtacaacttc 660
aacagccaca acgtctatat caccgccgac aagcagaaga acggcatcaa ggccaacttc 720
aagatccgcc acaacgtgga ggacggcagc gtgcagctcg ccgaccacta ccagcagaac 780
acccccatcg gcgacggccc cgtgctgctg cccgacaacc actacctgag cacccagtcc 840
gtgctgagca aagaccccaa cgagaagcgc gatcacatgg tcctgctgga gttcgtgacc 900
gccgccggga tcactcacgg catggacgag ctgtacaagg gtgggggtgg gagcggcggc 960
ggtggctccg cggccaacga tgaaaactat tctgaaaact atgcggatgc gtcttaatga 1020
tgatcggcac gtaagaggtt ccaactttca ccataatgaa ataagatcac taccgggcgt 1080
attttttgag ttatcgagat tttcaggagc taaggaagct aaaatggcta aactgacgtc 1140
ggccgttcca gtgcttactg cgcgtgatgt agcgggagcc gtagagtttt ggacggatcg 1200
tcttgggttt agtcgcgact ttgtggaaga tgacttcgca ggggttgttc gtgatgacgt 1260
cacactgttc atcagtgccg tacaggatca ggttgtaccc gataacactc ttgcgtgggt 1320
atgggtgcgt ggcctggatg agttatacgc cgaatggtcc gaggtagtca gcacaaactt 1380
ccgcgacgca tccgggcccg ctatgactga gatcggggaa caaccgtggg gacgtgagtt 1440
tgccttacgt gacccggcgg ggaactgcgt ccactttgtg gcggaggagc aggactaagg 1500
ataagtagtg gttgattgct aagttgtaaa tattttaacc cgccgttcat atggcgggtt 1560
gatttttata tgcctaaaca caaaaaattg taaaaataaa atccattaac agacctatat 1620
agatatttaa aaagaataga acagctcaaa ttatcagcaa cccaatactt tcaattaaaa 1680
acttcatggt agtcgcattt ataaccctat gaaaatgacg tctatctata ccccccctata 1740 ttttattcat catacaacaa attcatgata ccaataa 1777

<210> SEQ ID NO 20
<211> LENGTH: 898
<212> TYPE: DNA
<213> ORGANISM: Artificial Sequence
<220> FEATURE:
<223> OTHER INFORMATION: Synthetic

<400> SEQUENCE: 20
gaagtggaag aagcctggaa atgggtagac tccattactg aggcgtgggc gatggacaat 60
gatgcgccga aaccgtatca ggccggaacc tggggacccg ttgcctcggt ggcgatgatt 120
acccgtgatg gtcgttcctg gaatgagttt gaggcggcca acgatgaaaa ctattctgaa 180
aactatgcgg atgcgtctta atagttgaca attaatcatc ggcatagtat atcggcatag 240
tataatacga ctcactatag gagggccatc atgaagacct tcaacatctc tcagcaggat 300
ctggagctgg tggaggtcgc cactgagaag atcaccatgc tctatgagga caacaagcac 360
catgtcgggg cggccatcag gaccaagact ggggagatca tctctgctgt ccacattgag 420
gcctacattg gcagggtcac tgtctgtgct gaagccattg ccattgggtc tgctgtgagc 480
aacgggcaga aggactttga caccattgtg gctgtcaggc acccctactc tgatgaggtg 540
gacagatcca tcagggtggt cagcccctgt ggcatgtgca gagagctcat ctctgactat 600
gctcctgact gctttgtgct cattgagatg aatggcaagc tggtcaaaac caccattgag 660
gaactcatcc ccctcaagta caccaggaac taaagtaata tctgcgctta tcctttatgg 720
ttattttacc ggtaacatga tcttgcgcag attgtagaac aatttttaca ctttcaggcc 780
tcgtgcggat tcacccacga ggcttttttt attacactga ctgaaacgtt tttgccctat 840
gagctccggt tacaggcgtt tcagtcataa atcctctgaa tgaaacgcgt tgtgaatc 898

<210> SEQ ID NO 21
<211> LENGTH: 1675
<212> TYPE: DNA

<213> ORGANISM: Artificial Sequence
<220> FEATURE:
<223> OTHER INFORMATION: Synthetic

<400> SEQUENCE: 21
aacgtttgct gctggaaacc atgcgtggta ttcaggcact gtttgtacgt cgcgacgaag 60
tggaagaagc ctggaaatgg gtagactcca ttactgaggc gtgggcgatg gacaatgatg 120
cgccgaaacc gtatcaggcc ggaacctggg gacccgttgc ctcggtggcg atgattaccc 180
gtgatggtcg ttcctggaat gagtttgagg ggggttcagg cgggtcgggt ggcgtgagca 240
agggcgagga gctgttcacc ggggtggtgc ccatcctggt cgagctggac ggcgacgtaa 300
acggccacaa gttcagcgtg cgcggcgagg gcgagggcga tgccaccaac ggcaagctga 360
ccctgaagtt catctgcacc accggcaagc tgcccgtgcc ctggcccacc ctcgtgacca 420
ccctgaccta cggcgtgcag tgcttcagcc gctaccccga ccacatgaag cgccacgact 480
tcttcaagtc cgccatgccc gaaggctacg tccaggagcg caccatcagc ttcaaggacg 540
acggcaccta caagacccgc gccgaggtga agttcgaggg cgacaccctg gtgaaccgca 600
tcgagctgaa gggcatcgac ttcaaggagg acggcaacat cctggggcac aagctggagt 660
acaacttcaa cagccacaac gtctatatca ccgccgacaa gcagaagaac ggcatcaagg 720
ccaacttcaa gatccgccac aacgtggagg acggcagcgt gcagctcgcc gaccactacc 780
agcagaacac ccccatcggc gacggccccg tgctgctgcc cgacaaccac tacctgagca 840
cccagtccgt gctgagcaaa gaccccaacg agaagcgcga tcacatggtc ctgctggagt 900
tcgtgaccgc cgccgggatc actcacggca tggacgagct gtacaagtaa tgaatgatcg 960
gcacgtaaga ggttccaact ttcaccataa tgaaataaga tcactaccgg gcgtattttt 1020
tgagttatcg agattttcag gagctaagga agctaaaatg gccaagcctt tgtctcaaga 1080
agaatccacc ctcattgaaa gagcaacggc tacaatcaac agcatcccca tctctgaaga 1140
ctacagcgtc gccagcgcag ctctctctag cgacggccgc atcttcactg gtgtcaatgt 1200
atatcatttt actgggggac cttgtgcaga actcgtggtg ctgggcactg ctgctgctgc 1260
ggcagctggc aacctgactt gtatcgtcgc gatcggaaat gagaacaggg gcatcttgag 1320
cccctgcgga cggtgccgac aggtgcttct cgatctgcat cctgggatca aagccatagt 1380
gaaggacagt gatggacagc cgacggcagt tgggattcgt gaattgctgc cctctggtta 1440
tgtgtgggag ggctaagtag ggataacagg gtaattatct gcgcttatcc tttatggtta 1500
ttttaccggt aacatgatct tgcgcagatt gtagaacaat tttacactt tcaggcctcg 1560 tgcggattca cccacgaggc ttttttattt acactgactg aaacgttttt gccctatgag 1620
ctccggttac aggcgtttca gtcataaatc ctctgaatga aacgcgttgt gaatc 1675

<210> SEQ ID NO 22
<211> LENGTH: 1750
<212> TYPE: DNA
<213> ORGANISM: Artificial Sequence
<220> FEATURE:
<223> OTHER INFORMATION: Synthetic

<400> SEQUENCE: 22
aacgtttgct gctggaaacc atgcgtggta ttcaggcact gtttgtacgt cgcgacgaag 60
tggaagaagc ctggaaatgg gtagactcca ttactgaggc gtgggcgatg gacaatgatg 120
cgccgaaacc gtatcaggcc ggaacctggg gacccgttgc ctcggtggcg atgattaccc 180
gtgatggtcg ttcctggaat gagtttgagg ggggttcagg cgggtcgggt ggcgtgagca 240
agggcgagga gctgttcacc ggggtggtgc ccatcctggt cgagctggac ggcgacgtaa 300
acggccacaa gttcagcgtg cgcggcgagg gcgagggcga tgccaccaac ggcaagctga 360
ccctgaagtt catctgcacc accggcaagc tgcccgtgcc ctggcccacc ctcgtgacca 420
ccctgaccta cggcgtgcag tgcttcagcc gctaccccga ccacatgaag cgccacgact 480
tcttcaagtc cgccatgccc gaaggctacg tccaggagcg caccatcagc ttcaaggacg 540
acggcaccta caagacccgc gccgaggtga agttcgaggg cgacaccctg gtgaaccgca 600
tcgagctgaa gggcatcgac ttcaaggagg acggcaacat cctggggcac aagctggagt 660
acaacttcaa cagccacaac gtctatatca ccgccgacaa gcagaagaac ggcatcaagg 720
ccaacttcaa gatccgccac aacgtggagg acggcagcgt gcagctcgcc gaccactacc 780
agcagaacac ccccatcggc gacggccccg tgctgctgcc cgacaaccac tacctgagca 840
cccagtccgt gctgagcaaa gaccccaacg agaagcgcga tcacatggtc ctgctggagt 900
tcgtgaccgc cgccgggatc actcacggca tggacgagct gtacaagggt gggggtggga 960
gcggcggcgg tggctccgcg gccaacgatg aaaactattc tgaaaactat gcggatgcgt 1020
cttaatgaat gatcggcacg taagaggttc caactttcac cataatgaaa taagatcact 1080
accgggcgta ttttttgagt tatcgagatt ttcaggagct aaggaagcta aaatggccaa 1140
gcctttgtct caagaagaat ccaccctcat tgaaagagca acggctacaa tcaacagcat 1200
ccccatctct gaagactaca gcgtcgccag cgcagctctc tctagcgacg gccgcatctt 1260
cactggtgtc aatgtatatc attttactgg gggaccttgt gcagaactcg tggtgctggg 1320
cactgctgct gctgcggcag ctggcaacct gacttgtatc gtcgcgatcg gaaatgagaa 1380
caggggcatc ttgagcccct gcggacggtg ccgacaggtg cttctcgatc tgcatcctgg 1440
gatcaaagcc atagtgaagg acagtgatgg acagccgacg gcagttggga ttcgtgaatt 1500
gctgccctct ggttatgtgt gggagggcta agtagggata acagggtaat tatctgcgct 1560
tatcctttat ggttatttta ccggtaacat gatcttgcgc agattgtaga acaattttta 1620
cactttcagg cctcgtgcgg attcacccac gaggcttttt ttattacact gactgaaacg 1680
tttttgccct atgagctccg gttacaggcg tttcagtcat aaatcctctg aatgaaacgc 1740
gttgtgaatc 1750

<210> SEQ ID NO 23
<211> LENGTH: 1000
<212> TYPE: DNA
<213> ORGANISM: Artificial Sequence
<220> FEATURE:
<223> OTHER INFORMATION: Synthetic

<400> SEQUENCE: 23
gcggcgagct gctgggtgaa atcggcctgg caatcgaaat gggttgtgat gctgaagaca 60
tcgcactgac catccacgcg cacccgactc tgcacgagtc tgtgggcctg gcggcagaag 120
tgttcgaagg tagcattacc gacctgccga acccgaaagc gaagaagaag gcggccaacg 180
atgaaaacta ttctgaaaac tatgcggatg cgtcttaata gcgaatccat gtgggagttt 240
attcttgaca cagatattta tgatataata actgagtaag cttaacataa ggaggaaaaa 300
catatgttac gcagcagcaa cgatgttacg cagcagggca gtcgccctaa aacaaagtta 360
ggtggctcaa gtatgggcat cattcgcaca tgtaggctcg gccctgacca agtcaaatcc 420
atgcgggctg ctcttgatct tttcggtcgt gagttcggag acgtagccac ctactcccaa 480
catcagccgg actccgatta cctcgggaac ttgctccgta gtaagacatt catcgcgctt 540
gctgccttcg accaagaagc ggttgttggc gctctcgcgg cttacgttct gcccaagttt 600
gagcagccgc gtagtgagat ctatatctat gatctcgcag tctccggcga gcaccggagg 660
cagggcattg ccaccgcgct catcaatctc ctcaagcatg aggccaacgc gcttggtgct 720
tatgtgatct acgtgcaagc agattacggt gacgatcccg cagtggctct ctatacaaag 780
ttgggcatac gggaagaagt gatgcacttt gatatcgacc caagtaccgc cacctaattt 840
ttcgtttgcc ggaacatccg gcaattaaaa aagcggctaa ccacgccgct ttttttacgt 900
ctgcaattta cctttccagt cttcttgctc cacgttcaga gagacgttcg catactgctg 960
accgttgctc gttattcagc ctgacagtat ggttactgtc 1000

<210> SEQ ID NO 24
<211> LENGTH: 15
<212> TYPE: DNA
<213> ORGANISM: Artificial Sequence
<220> FEATURE:
<223> OTHER INFORMATION: Synthetic

<400> SEQUENCE: 24
gggagaccac aacgg 15

<210> SEQ ID NO 25
<211> LENGTH: 16
<212> TYPE: DNA
<213> ORGANISM: Artificial Sequence
<220> FEATURE:
<223> OTHER INFORMATION: Synthetic

<400> SEQUENCE: 25
cgcagtcgaa cgaccg 16

<210> SEQ ID NO 26
<211> LENGTH: 94
<212> TYPE: DNA
<213> ORGANISM: Artificial Sequence
<220> FEATURE:
<223> OTHER INFORMATION: Synthetic

<400> SEQUENCE: 26
tcgagttccc cgcgccagcg gggataaacc gtattgacca attcattcgg gacagttatt 60
agttcgagtt ccccgcgcca gcggggataa accg 94

<210> SEQ ID NO 27
<211> LENGTH: 59
<212> TYPE: DNA
<213> ORGANISM: Artificial Sequence
<220> FEATURE:
<223> OTHER INFORMATION: Synthetic

<400> SEQUENCE: 27
gggacagtta ttagttcgag ttccccgcgc cagcggggat aaaccgaaaa aaaaaacccc 59

<210> SEQ ID NO 28
<211> LENGTH: 63
<212> TYPE: DNA
<213> ORGANISM: Artificial Sequence
<220> FEATURE:
<223> OTHER INFORMATION: Synthetic

<400> SEQUENCE: 28
gaatgaattg gtcaatacgg tttatccccg ctggcgcggg gaactcgagg tggtaccaga 60
tct 63

<210> SEQ ID NO 29
<211> LENGTH: 92
<212> TYPE: DNA
<213> ORGANISM: Artificial Sequence
<220> FEATURE:
<223> OTHER INFORMATION: Synthetic

<400> SEQUENCE: 29
tcgagttccc cgcgccagcg gggataaacc gagtggttgc tggataactt tacgggcatg 60
ctcgagttcc ccgcgccagc ggggataaac cg 92

<210> SEQ ID NO 30
<211> LENGTH: 60
<212> TYPE: DNA
<213> ORGANISM: Artificial Sequence
<220> FEATURE:
<223> OTHER INFORMATION: Synthetic

<400> SEQUENCE: 30
aactttacgg gcatgctcga gttccccgcg ccagcgggga taaaccgaaa aaaaaacccc 60

<210> SEQ ID NO 31
<211> LENGTH: 60
<212> TYPE: DNA
<213> ORGANISM: Artificial Sequence
<220> FEATURE:
<223> OTHER INFORMATION: Synthetic

<400> SEQUENCE: 31
atccagcaac cactcggttt atccccgctg gcgcggggaa ctcgaggtgg taccagatct 60

<210> SEQ ID NO 32
<211> LENGTH: 92
<212> TYPE: DNA
<213> ORGANISM: Artificial Sequence
<220> FEATURE:
<223> OTHER INFORMATION: Synthetic

<400> SEQUENCE: 32
tcgagttccc cgcgccagcg gggataaacc gctcgtaaaa gcagtacagt gcaccgtaag 60
atcgagttcc ccgcgccagc ggggataaac cg 92

<210> SEQ ID NO 33
<211> LENGTH: 59
<212> TYPE: DNA
<213> ORGANISM: Artificial Sequence
<220> FEATURE:
<223> OTHER INFORMATION: Synthetic

<400> SEQUENCE: 33
cagtgcaccg taagatcgag ttccccgcgc cagcggggat aaaccgaaaa aaaaacccc 59

<210> SEQ ID NO 34
<211> LENGTH: 60
<212> TYPE: DNA
<213> ORGANISM: Artificial Sequence
<220> FEATURE:
<223> OTHER INFORMATION: Synthetic

<400> SEQUENCE: 34
tactgctttt acgagcggtt tatccccgct ggcgcgggga actcgaggtg gtaccagatc 60

<210> SEQ ID NO 35
<211> LENGTH: 155
<212> TYPE: DNA
<213> ORGANISM: Artificial Sequence
<220> FEATURE:
<223> OTHER INFORMATION: Synthetic

<400> SEQUENCE: 35
tcgagttccc cgcgccagcg gggataaacc gtattgacca attcattcgg gacagttatt 60
agttcgagtt ccccgcgcca gcggggataa accgctcgta aaagcagtac agtgcaccgt 120
aagatcgagt tccccgcgcc agcggggata aaccg 155

<210> SEQ ID NO 36
<211> LENGTH: 30
<212> TYPE: DNA
<213> ORGANISM: Artificial Sequence
<220> FEATURE:
<223> OTHER INFORMATION: Synthetic

<400> SEQUENCE: 36
gcgccagcgg ggataaaccg ctcgtaaaag 30

<210> SEQ ID NO 37
<211> LENGTH: 28
<212> TYPE: DNA
<213> ORGANISM: Artificial Sequence
<220> FEATURE:
<223> OTHER INFORMATION: Synthetic

<400> SEQUENCE: 37
cttgcccgcc tgatgaatgc tcatccgg 28

<210> SEQ ID NO 38
<211> LENGTH: 28
<212> TYPE: DNA
<213> ORGANISM: Artificial Sequence
<220> FEATURE:
<223> OTHER INFORMATION: Synthetic

<400> SEQUENCE: 38
ccggatgagc attcatcagg cgggcaag 28

<210> SEQ ID NO 39
<211> LENGTH: 44
<212> TYPE: DNA
<213> ORGANISM: Artificial Sequence
<220> FEATURE:
<223> OTHER INFORMATION: Synthetic

<400> SEQUENCE: 39
cggtttatcc ccgctggcgc ggggaactcg aactaataac tgtc 44

<210> SEQ ID NO 40
<211> LENGTH: 75
<212> TYPE: DNA
<213> ORGANISM: Artificial Sequence -continued

```
<220> FEATURE:
<223> OTHER INFORMATION: Synthetic

<400> SEQUENCE: 40

tacagggatc cagttatcaa taagcaaatt catttgttct ccttcatatg atcaaaggga     60

aaactgtcca tatgc                                                      75
```